US012636433B2

(12) United States Patent
Alheidt et al.

(10) Patent No.: US 12,636,433 B2
(45) Date of Patent: May 26, 2026

(54) SYSTEM AND METHOD FOR BUTTERFLY NEEDLE ASSEMBLY

(71) Applicant: KORU Medical Systems, Inc., Mahwah, NJ (US)

(72) Inventors: Thomas Alan Alheidt, Sussex, NJ (US); Donald Fraser Vanroyen, Philadelphia, PA (US); Robert Gregory Hoff, Boonton, NJ (US); Joseph Duane Barone, Jr., Scottsdale, AZ (US); Brian Christopher Case, Lake Villa, IL (US)

(73) Assignee: KORU Medical Systems, Inc., Mahwah, NJ (US)

( * ) Notice: Subject to any disclaimer, the term of this patent is extended or adjusted under 35 U.S.C. 154(b) by 537 days.

(21) Appl. No.: 18/216,342

(22) Filed: Jun. 29, 2023

(65) Prior Publication Data
US 2025/0001072 A1      Jan. 2, 2025

(51) Int. Cl.
*A61M 5/158*        (2006.01)
*A61M 5/32*         (2006.01)

(52) U.S. Cl.
CPC .......... *A61M 5/158* (2013.01); *A61M 5/3204* (2013.01); *A61M 5/3293* (2013.01); *A61M 2005/1585* (2013.01)

(58) Field of Classification Search
CPC .. A61M 5/158; A61M 5/3204; A61M 5/3293; A61M 2005/1585
(Continued)

(56) References Cited

U.S. PATENT DOCUMENTS 5,951,522 A * 9/1999 Rosato .............. A61M 25/0637
                                                      604/162
6,436,073 B1  8/2002 Von Teichert
                    (Continued)

FOREIGN PATENT DOCUMENTS

KR    10-2023-0076944      6/2023

OTHER PUBLICATIONS

PCT International Search Report for International Application PCT/US2023/026725, search report data of mailing Mar. 27, 2024 (Mar. 27, 2024).

*Primary Examiner* — Phillip A Gray
(74) *Attorney, Agent, or Firm* — Daniel W. Roberts; Law Offices of Daniel W. Roberts, LLC

(57) ABSTRACT
Provided is a butterfly needle assembly, including: a flexible member having a central region with a first side member and a second side member collectively providing a generally flat bottom, the central region having a middle area; an adhesive dressing disposed upon the generally flat bottom, the adhesive dressing protected by a removable cover; a needle hub disposed within the central region, the needle hub receiving a flexible tubing line generally parallel to the generally flat bottom and providing a needle extending generally normal to the generally flat bottom from the middle area of the central region, the needle extending for a first length; a removable needle cover initially disposed about the needle, the removable needle cover structured and arranged to removably engage with the needle hub; and a closing system structured and arranged to close the first side member and the second side member of the flexible member about the needle. A method of making a butterfly needle assembly is also provided.

49 Claims, 21 Drawing Sheets

(58) Field of Classification Search
USPC ...................................................... 604/93.01
See application file for complete search history.

(56)                     References Cited

U.S. PATENT DOCUMENTS

| | | | |
|---|---|---|---|
| 6,991,020 B1 | 1/2006 | Cheng | |
| 8,157,770 B2 | 4/2012 | Elwell et al. | |
| 8,876,777 B2 | 11/2014 | Bruggger et al. | |
| 8,961,476 B2* | 2/2015 | Lambert | A61M 5/3243 |
| | | | 604/177 |
| 10,420,886 B2 | 9/2019 | Sealfon | |
| 10,500,389 B2 | 12/2019 | Sealfon et al. | |
| 10,799,839 B1 | 10/2020 | Brookins | |
| 2002/0111581 A1* | 8/2002 | Sasso | A61M 5/158 |
| | | | 604/93.01 |
| 2005/0090783 A1 | 4/2005 | Sibbit, Jr. | |
| 2008/0177234 A1 | 7/2008 | Keaton et al. | |
| 2009/0287115 A1 | 11/2009 | Abbott | |
| 2009/0306602 A1 | 12/2009 | Elwell et al. | |
| 2011/0208102 A1 | 8/2011 | Chawki | |
| 2011/0295207 A1 | 12/2011 | Brugger et al. | |
| 2015/0342639 A1* | 12/2015 | Wang | A61M 5/158 |
| | | | 604/263 |
| 2017/0281858 A1 | 10/2017 | Imran | |
| 2021/0046241 A1 | 2/2021 | Rousche | |
| 2022/0265923 A1 | 8/2022 | Sealfon | |
| 2023/0190157 A1 | 6/2023 | Bullington et al. | |

* cited by examiner

SYSTEM AND METHOD FOR BUTTERFLY NEEDLE ASSEMBLY

FIELD OF THE INVENTION

The present invention relates generally to systems and methods for subcutaneous infusion systems and equipment, and more particularly needle assemblies which provide a flexible member for stabilizing and protecting the needle when disposed into the tissues of a patient, and systems to reduce the opportunity for accidental needle stick before and after use, the assembly also providing ease of assembly for a variety of different needle gauges with a common flexible member element as well as sterilization prior to use.

BACKGROUND

Infusion systems for the delivery of liquid pharmaceuticals are widely used and relied upon by patients and care givers alike.

With a typical injection, commonly referred to as a "shot" a patient is quickly injected with a medicant provided by a handheld syringe directly connected to a needle. The caregiver punctures the patient's skin with the needle to reach desired tissues or structures, depresses the plunger of the syringe to inject the medicant, and then withdraws the needle. This process is typically performed in less than one minute.

With an infusion, typically the medicant is delivered over a period of time. The needle is inserted to reach the desired tissues or structures and then remains in contact with those tissues or structures for the duration of the treatment which is typically measurable in many minutes or hours.

One form of infusion therapy is Immuno Globulin (Ig) therapy, and it is frequently used to improve the quality of life for patients with conditions such as Primary Immune Deficiency (PID), Secondary Immune Deficiency (SID), Chronic Inflammatory Demyelinating Polyradiculoneuropathy (CIPD), and Severe Combined Immunodeficiency (SCID). Historically, Ig therapy has been administered intravenously (IVIg) every 3-4 weeks, which can result in inconsistent serum levels and burdensome infusion experiences for patients.

Subcutaneous Ig therapy (SCIg) is a more convenient option that allows for consistent serum levels and can be done at home. However, SCIg has its own challenges, such as the need for patients to prepare and administer the infusions themselves and potential site leakage during infusions. This device will administer therapy subcutaneously through single or multiple injection sites depending on the drug volumes prescribed.

While important in any medical setting, for home use, it is quite important that the infusion needle system assembly in particular be as simple and straightforward to use as possible.

To assist with ensuring that the needle reaches the desired tissues or structures, infusion needles are often provided in specific lengths. In addition, to help anchor the needle during the infusion procedure, these needles often have an anchor of sorts, from which the needle extends, and which is taped in place upon a patient once the needle element has been disposed into their tissues.

To further minimize the possibility of disturbing the needle, in many cases a needle bent to a 900 is used, so that medicant supply tubing is essentially parallel to the patient's skin, and capable of being taped in place while the delivery end of the needle is perpendicular to the skin and at the desired pre-determined depth. Fabrication of 900 is more involved than fabrication of straight needles, so desirable as such a configuration may be for an infusion butterfly needle, additional cost is typically necessary.

Two other issues are also common—maintaining sterility of the needle before use and avoidance of accidental needle stick before and after use. There have been various efforts to address at least the needle stick issue. U.S. Pat. No. 6,911, 020 to Raines teaches a Huber Needle With Folding Safety Wings. A 900 Huber needle is mounted with the horizontal portion of the needle disposed within a hub such that the perpendicular portion of the needle extends away from the hub and is mostly between a pair of folding wings. Although the entire Raines assembly may be provided in a hermetically sealed bag, once opened, all elements of the Rains assembly are exposed to the elements including the needle. In addition, as the hub is formed about the horizontal portion of the needle, to provide different needle gauges requires an entirely different casting and assembly process.

U.S. Pat. No. 5,951,522 to Rosato et al., entitled Hypodermic Needle Safety Enclosure teaches a similar device. Here again, a 90° Huber needle is partially enclosed by a wing structure. When disposed upon a patient at an insertion site, the wing elements fold up and apart to allow the needle to be exposed and disposed into the patient. The wings then also provide a generally flat surface over which tape may be affixed to secure the needle assembly during infusion. When removed, the wing elements unfold about the needle once again. So while attentive to before and after use needle stick mitigation, Rosato is again silent with respect to maintaining sterility of the needle prior to use.

Another reference is US Patent Publication 2008/0177234 to Keaton et al., entitled Safety Subcutaneous Infusion Set. Keaton teaches a butterfly anchor formed with a central body from which the needle extends and a pair of folding wings. When the wings are folded together about the needle, a locking post may be inserted into a hole at the distal tip of one wing for locking the wings together. The Keaton abstract notes, "[t]hus, the wings can be conveniently folded over the catheter and latched in place to protect the user from pricking after use." Keaton also discloses that the assembly may be held in place by an adhesion strip placed overtop the assembly. But as with Raines, there is no teaching for how sterility of the device is maintained, and the issue of preventing needle sticks is an after-use issue.

Yet another reference is U.S. Pat. No. 8,961,476 to Lambert entitled Sharps Protector Device For Protecting A User From A Sharp Tip OF A Medical Needle. As taught by Lambert, a needle extends perpendicularly from a central body portion from which also extend a pair of wings. A mechanical fastener is disposed on at least one wing of the pair of wings, the mechanical fastener configured to selectively attach the pair of wings together with the medial needle positioned therebetween so as to protect against accidental needle stick injury. Lambert specifically teaches that the mechanical fastener includes a lip extending along at least a portion of a perimeter of at least one wing of the pair of wings and a mating portion along a perimeter of at least one other wing of the pair of wings, and wherein the mating portion and the lip are configured to align the at least one wing relative to the at least one other wing in the closed position. Lambert also teaches that a wing may further include a groove to house at least a portion of the needle when the wings are in the closed position. So as with the other references of Raines, Rosato and Keaton, the only form of needle protection against needle stick taught by Lambert is provided by the wings of the assembly, and there is no teaching of providing sterility before use.

Moreover, while perhaps advantageous in their own right for specific issues, all of these references fall victim to common issues. For those using 900 needle, the complexity of their formation mandates an increased cost over that of straight needles. Further, each assembly is distinct for a specific needle gauge, so to provide a range of needle gauge options a complete inventory must be fabricated for each desired needle gauge—thus requiring storage space for each option, and for those of lesser frequency of use, an issue of shelf life may develop as well.

And further, these assemblies are affixed to the patient by adhesive strips placed over the assembly once it has been placed to dispose the needle into the patient. This requires separate adhesive strips, if not also release of the assembly to retrieve the strips and then affix them in place. Of course, releasing the assembly while it is disposed into a patient prior to the application of the adhesion strips permits an opportunity for the assembly to be moved should the patient move, or a person catch the supply tubing.

And yet further, many of the above noted devices have hard or relatively hard elements, such as the folding wings. As such these hard elements do not easily conform to the patient's skin, and indeed may press into, or even bite into the patient's skin when the assembly is taped into place. As such, patient discomfort may result.

Hence there is a need for a method and system that is capable of overcoming one or more of the above identified challenges.

SUMMARY OF THE INVENTION

Our invention solves the problems of the prior art by providing a novel configurable flow controller, kit and method of use therefore.

In particular, and by way of example only, according to one embodiment of the present invention, provided is a butterfly needle assembly, including: a flexible member having a central region with a first side member and a second side member collectively providing a generally flat bottom, the central region having a middle area; an adhesive disposed upon the generally flat bottom, the adhesive protected by a removable cover; a needle hub disposed within the central region, the needle hub receiving a flexible tubing line generally parallel to the generally flat bottom and providing a needle extending generally normal to the generally flat bottom from the middle area of the central region, the needle extending for a first length; a removable needle cover initially disposed about the needle, the removable needle cover structured and arranged to removably engage with the needle hub; and a closing system structured and arranged to close the first side member and the second side member of the flexible member about the needle.

For yet another embodiment, provided is a butterfly needle assembly, including: a flexible member having a central region with a first side member and a second side member collectively providing a generally flat bottom; an adhesive disposed upon the generally flat bottom, the adhesive protected by a removable cover; a needle hub frame united with the flexible member opposite from the adhesive; a snap-in needle structure provided by a duct member having a first end and a second end, the first end joined with a flexible tubing line and the second end joined with a needle having a first length, the second end generally normal to the first end, the duct member further structured and arranged for snap-in binding with the needle hub frame, the needle extending generally normal to the generally flat bottom from a middle area of the central region, the flexible tubing generally parallel to the generally flat bottom proximate to the first end of the duct member; and a removable needle cover initially disposed about the needle, the removable needle cover structured and arranged to removably engage with the needle hub frame; and a closing system structured and arranged to close the first side member and the second side member of the flexible member about the needle.

In yet another embodiment, provided is a butterfly needle assembly, including: a flexible member having a central region with a first side member and a second side member collectively providing a generally flat bottom, a button disposed upon the generally flat bottom proximate to a first distal edge of the first side member and a through-hole disposed proximate to a second distal edge of the second side member, the button and through-hole collectively providing a closing system structured and arranged to close the first side member and the second side member of the flexible member about the needle; an adhesive disposed upon the generally flat bottom, the adhesive protected by a removable cover; a needle hub frame united with the flexible member opposite from the adhesive; a snap-in needle structure provided by a duct member having a first end and a second end, the first end joined with a flexible tubing line and the second end joined with a needle having a first length, the second end generally normal to the first end, the duct member further structured and arranged for snap-in binding with the needle hub frame, the needle extending generally normal to the generally flat bottom from the central region, the flexible tubing generally parallel to the generally flat bottom proximate to the first end of the duct member; and a removable needle cover initially disposed about the needle, the removable needle cover having a first end disposed through the generally flat bottom into the needle hub frame, the first end having opposing side tabs structured and arranged to rotatably lock into the needle hub frame.

And, still further, for yet another embodiment, provided is a method of providing a butterfly needle assembly, including: providing a flexible member having a central region with a first side member and a second side member collectively providing a generally flat bottom, the central region having a middle area; providing an adhesive upon the generally flat bottom, the adhesive protected by a removable cover; providing a needle hub disposed within the central region, the needle hub receiving a flexible tubing line generally parallel to the generally flat bottom and providing a needle extending generally normal to the generally flat bottom from the middle area of the central region, the needle extending for a first length; providing a removable needle cover initially disposed about the needle, the removable needle cover structured and arranged to removably engage with the needle hub; and providing a closing system structured and arranged to the first side member and the second side member of the flexible member about the needle.

BRIEF DESCRIPTION OF THE DRAWINGS

FIG. 2B is a front, lower perspective view of the flexible member of the butterfly needle assembly shown in FIGS. 1A-1F in accordance with at least one embodiment of the present invention;

FIG. 5B is a top plane view of the removable needle cover shown in FIG. 1A in accordance with at least one embodiment of the present invention;

FIG. 5C is a side plane view of the removable needle cover shown in FIG. 1A in accordance with at least one embodiment of the present invention;

FIG. 5D is a front plane view of the removable needle cover shown in FIG. 1A in accordance with at least one embodiment of the present invention;

DETAILED DESCRIPTION

Before proceeding with the detailed description, it is to be appreciated that the present teaching is by way of example only, not by limitation. The concepts herein are not limited to use or application with a specific system or method for providing a system or method for a butterfly needle assembly. Thus, although the instrumentalities described herein are for the convenience of explanation shown and described with respect to exemplary embodiments, it will be understood and appreciated that the principles herein may be applied equally in other types of injection or infusion needle assembly systems and methods.

This invention is described with respect to preferred embodiments in the following description with reference to the Figures, in which like numbers represent the same or similar elements. Further, with the respect to the numbering of the same or similar elements, it will be appreciated that the leading values identify the Figure in which the element is first identified and described, e.g., element 100 appears in FIG. 1.

Figure 1A:
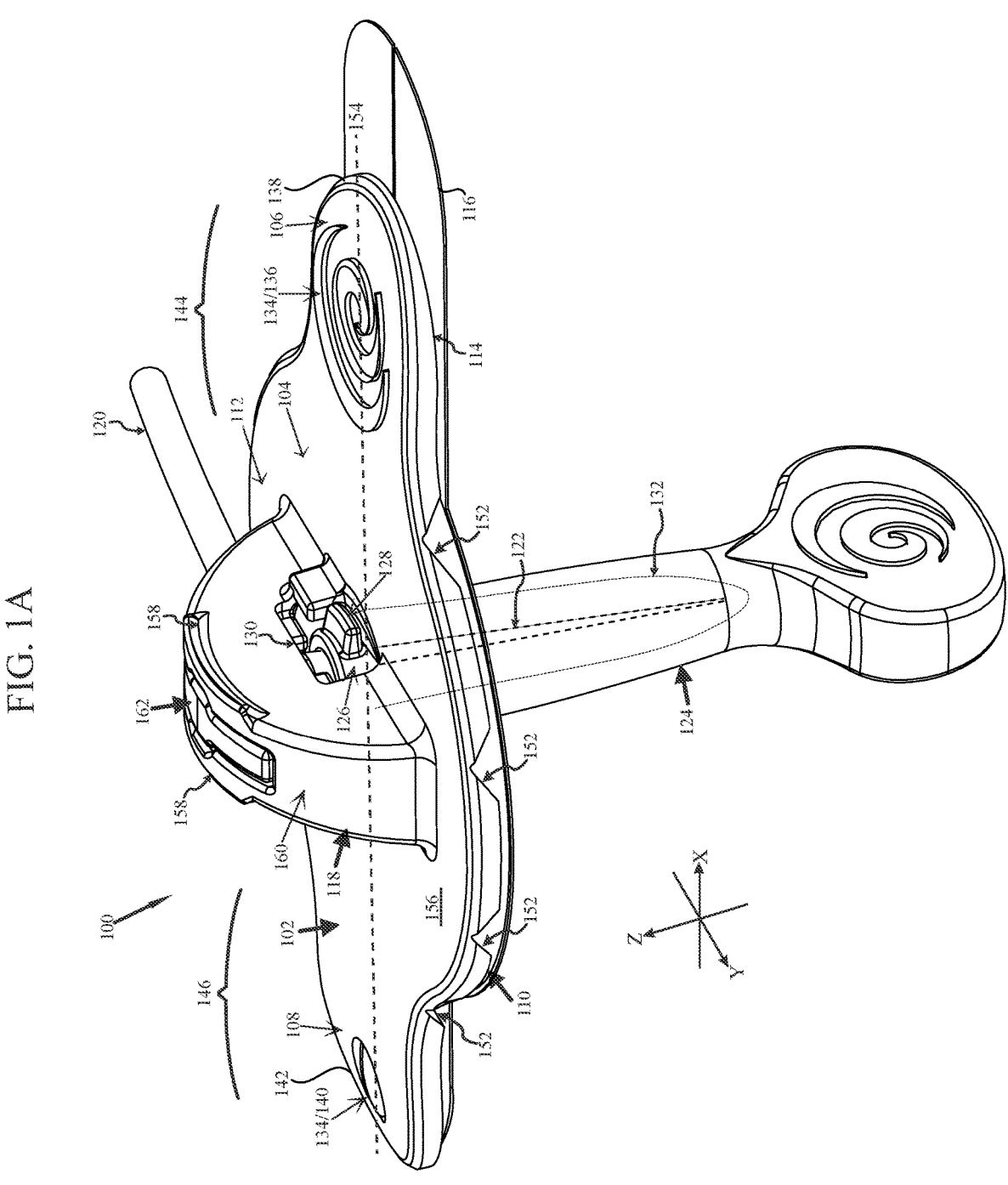
FIG. 1A is a front, upper perspective view of a butterfly needle assembly in accordance with at least one embodiment of the present invention.

Turning now to the drawings, and more specifically FIGS. 1A-1G there is shown at least one butterfly needle assembly 100, hereinafter BNA 100, in accordance with at least one embodiment of the present invention. FIG. 1A presents a top perspective view of BNA 100, with FIG. 1B providing a bottom perspective view, and FIGS. 1C, 1D and 1E respectively providing a perspective side, plain front and plain top view of BNA 100.

Figure 1B:
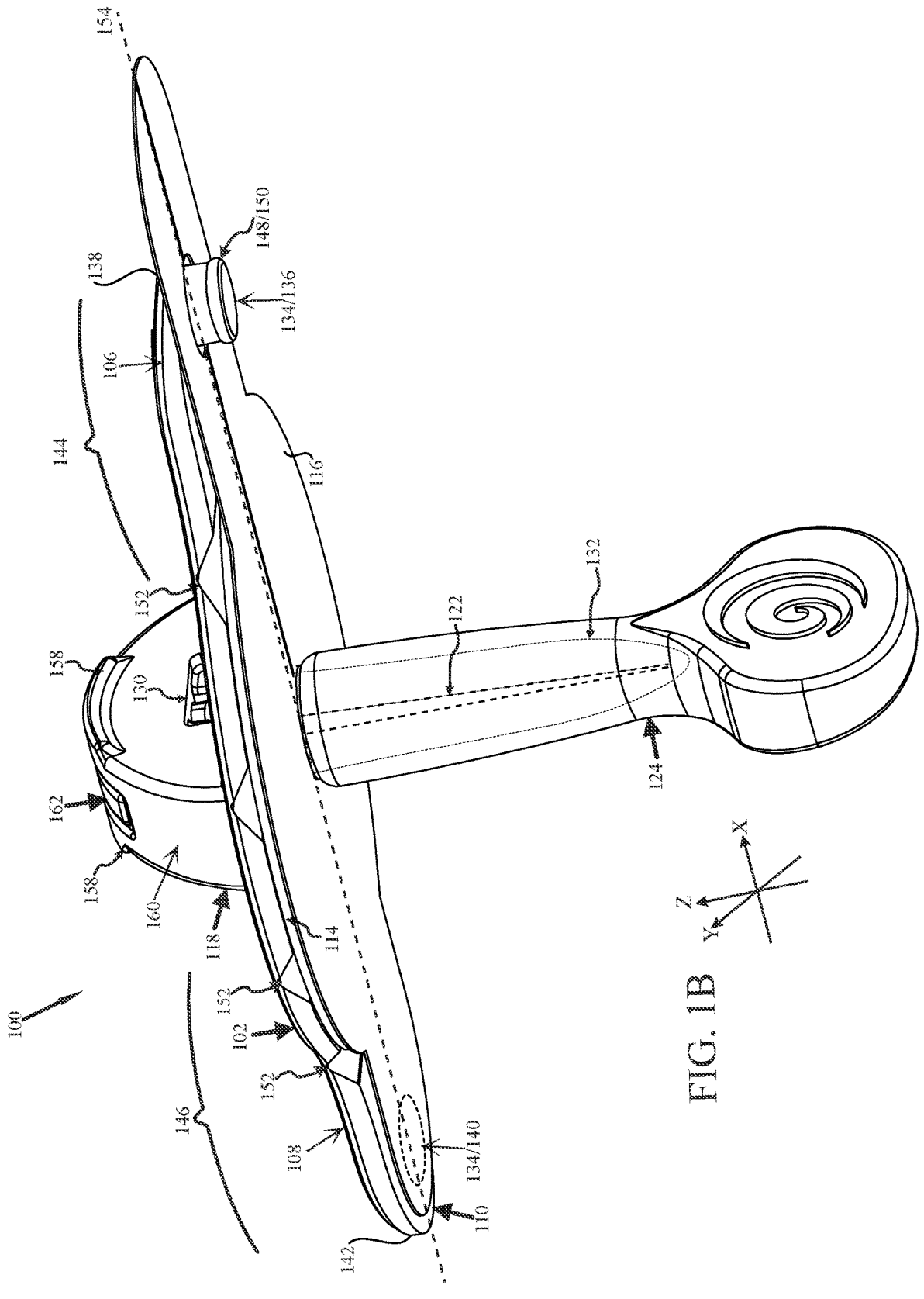
FIG. 1B is a front, lower perspective view of a butterfly needle assembly in accordance with at least one embodiment of the present invention.
Figure 1C:
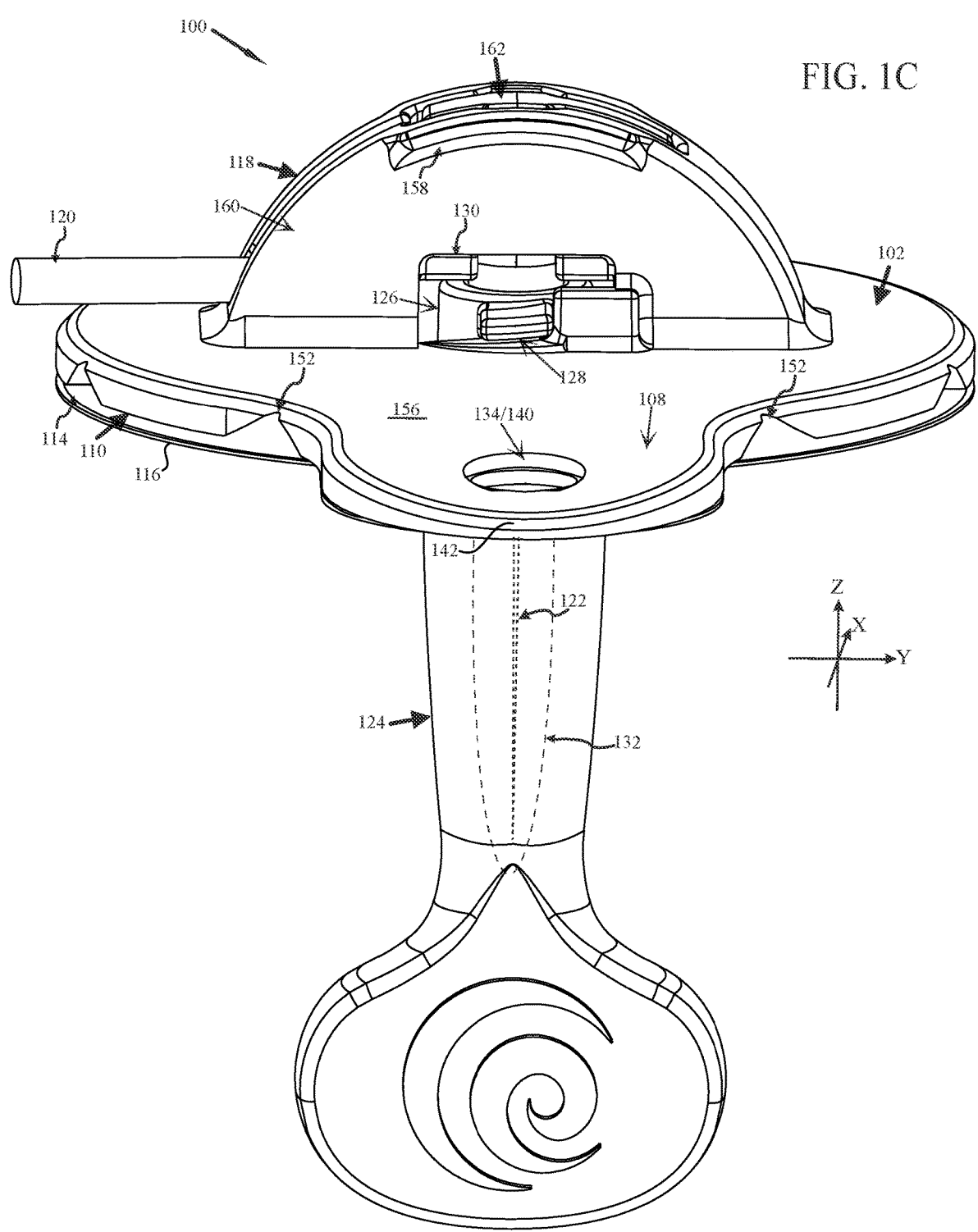
FIG. 1C is a side perspective view of a butterfly needle assembly in accordance with at least one embodiment of the present invention.
Figure 1D:
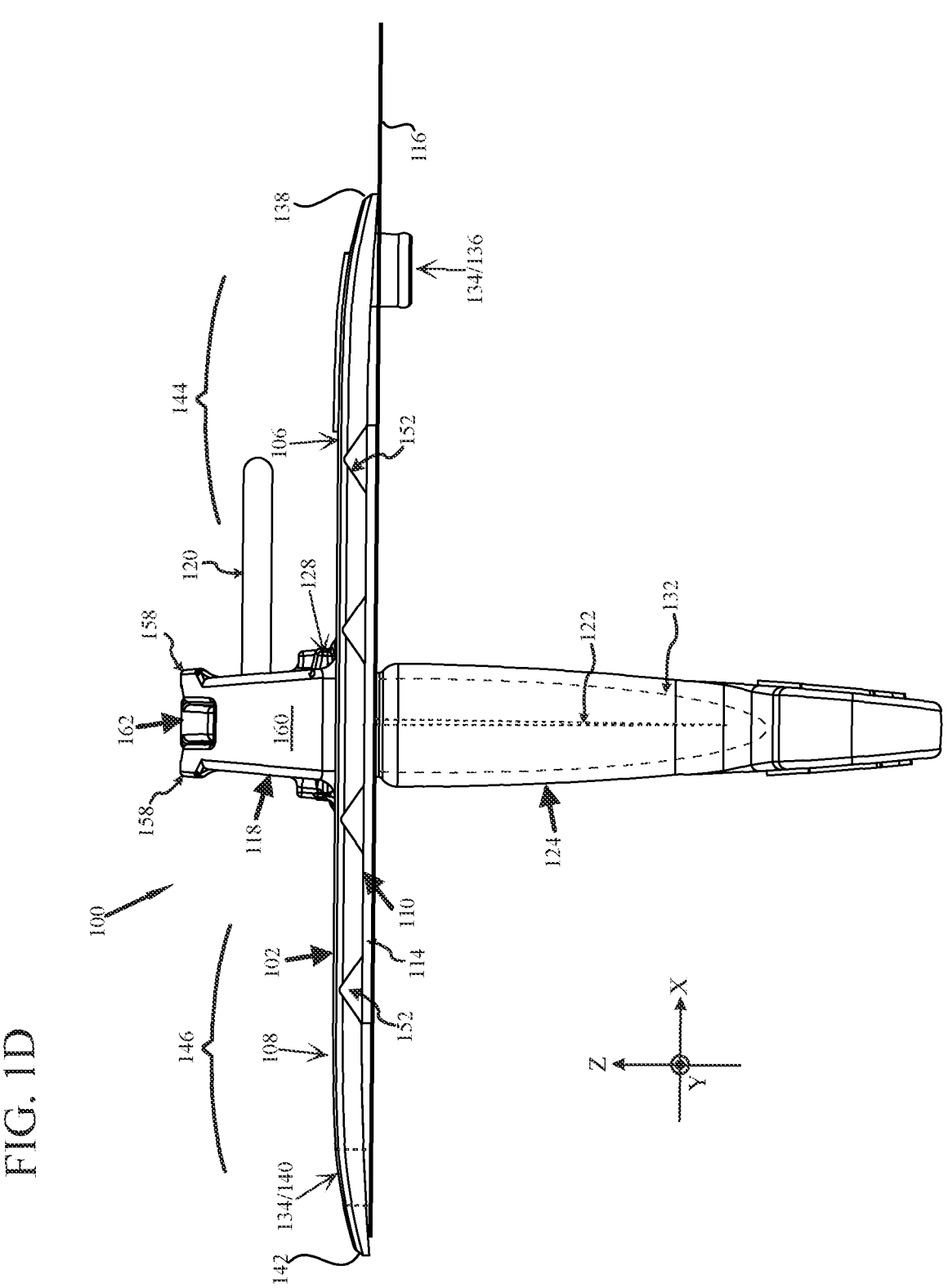
FIG. 1D is a front plane view of a butterfly needle assembly in accordance with at least one embodiment of the present invention.
Figure 1E:
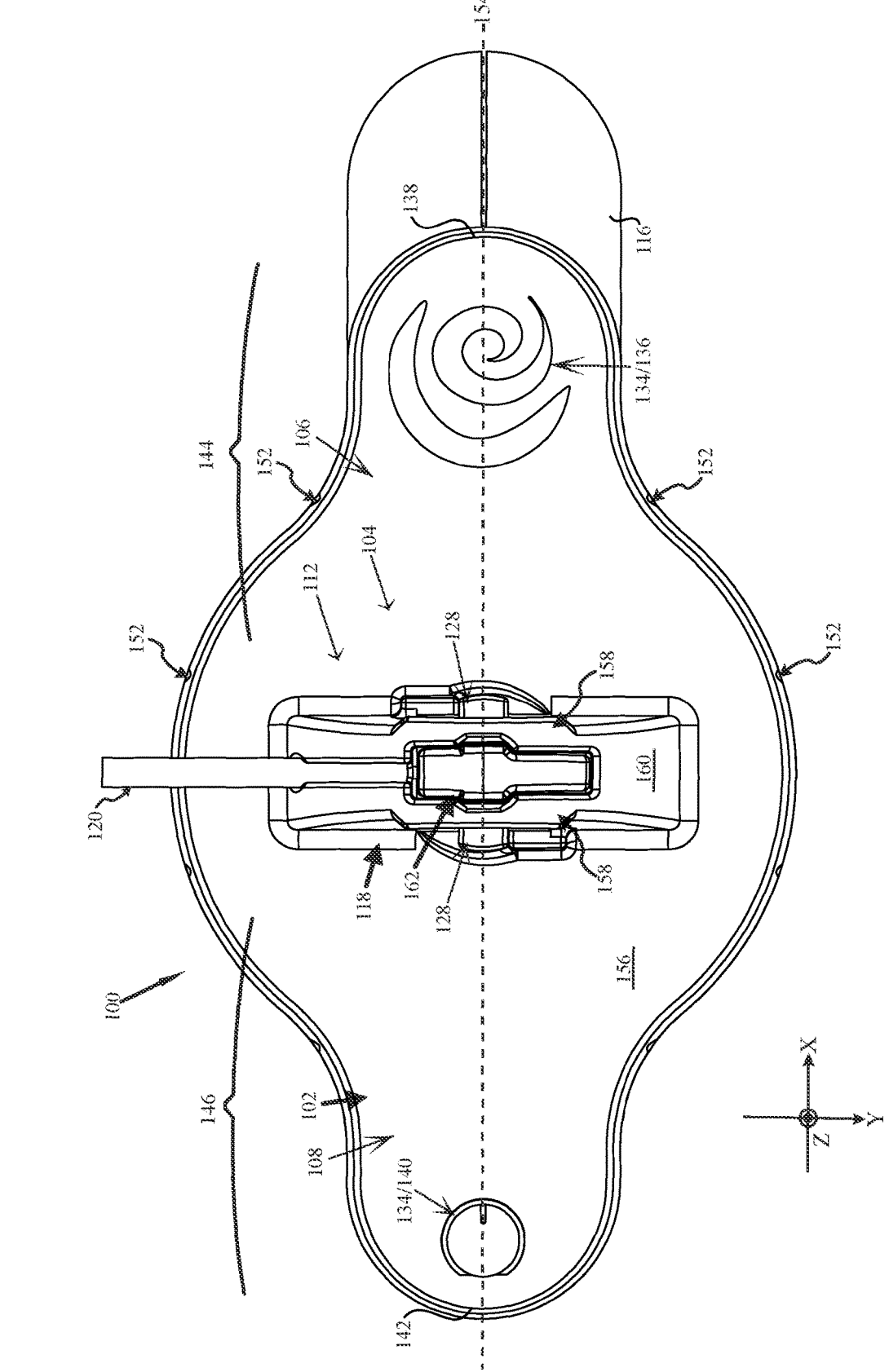
FIG. 1E is a top plane view of a butterfly needle assembly in accordance with at least one embodiment of the present invention.
Figure 1F:
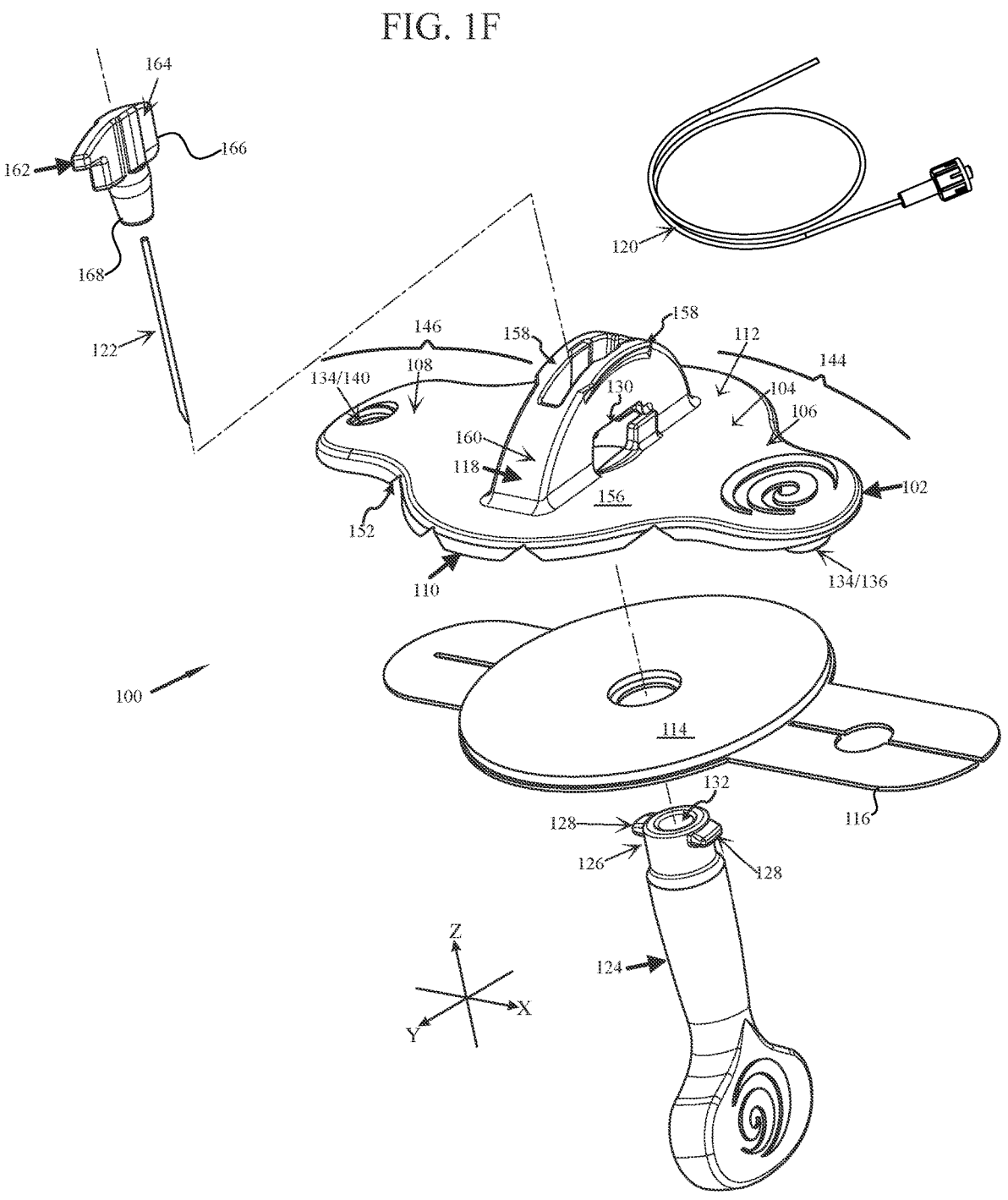
FIG. 1F is upper perspective exploded view of a butterfly needle assembly in accordance with at least one embodiment of the present invention.
Figure 1G:
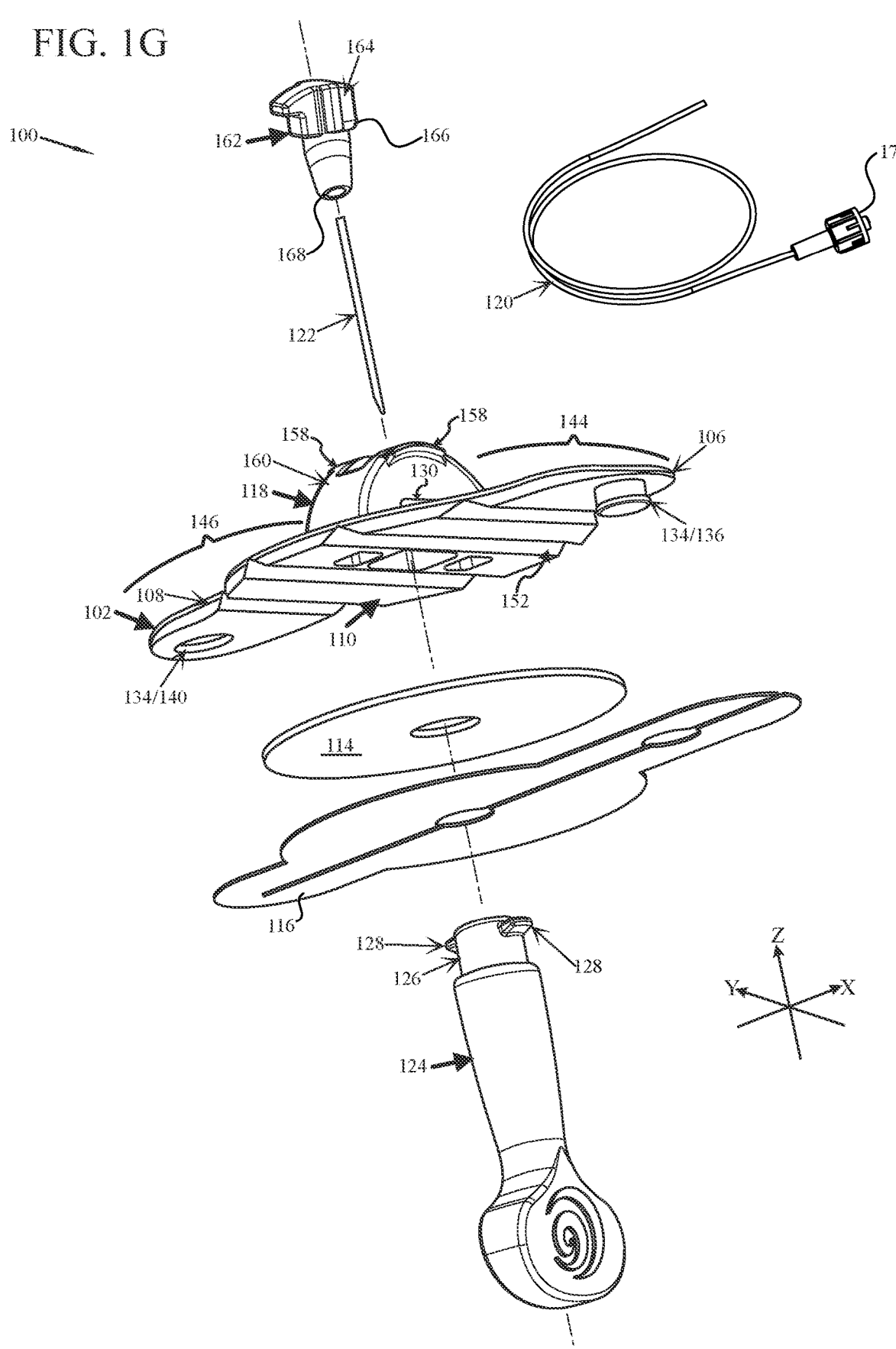
FIG. 1G is a lower perspective exploded view of a butterfly needle assembly in accordance with at least one embodiment of the present invention.

FIGS. 1F and 1G in connection with FIGS. 1A-1E, provide top and bottom perspective exploded views which may be appreciated to assist with understanding the configuration and placement of the elements comprising BNA 100.

To facilitate the description of systems and methods for embodiments of BNA 100, the orientation of BNA 100 as presented in the figures is referenced to the coordinate system with three axes orthogonal to one another as shown in FIG. 1. The axes intersect mutually at the origin of the coordinate system, which is chosen to be the center of BNA 100, however the axes shown in all figures are offset from their actual locations for clarity and ease of illustration.

As shown, BNA 100 is generally provided by a plurality of elements, the most specific of which is perhaps the flexible member 102, which provides a unibody design permitting ease of assembly and improved patient comfort during insertion and throughout the duration of the infusion session. The flexible member 102 has a central region 104 with a first side member 106 and a second side member 108 which collectively provide a generally flat bottom 110. The central region 104 will also be appreciated to have a middle area 112. As used herein, the term "flexible" as applied to the flexible member 102 is understood and appreciated to mean that the flexible member 102 is relatively pliable and will easily conform to a patient's skin when and where BNA 100 is disposed upon the patient's body for treatment.

For at least one embodiment, BNA 100 is provided with an adhesive 114 disposed upon the generally flat bottom 110, the adhesive 114 initially protected by a removable cover 116. In varying embodiments, the adhesive 114 may be provided to substantially all of the generally flat bottom 110, or generally the portion of the generally flat bottom 110 of the central region 104. The adhesive 114 may be applied to all or a portion of the generally flat bottom 110 as a spray-on layer, as a cutting from a roll or sheet, by dipping, or other method of application and/or layer development. In addition, for at least one embodiment the generally flat bottom 110 may be textured to provide an increased bonding surface or bonding strength of the adhesive 114.

Moreover, in varying embodiments, the adhesive 114 may be appreciated as an element/component of the generally flat bottom 110 or as an adapted adhesive dressing that is joined to the bottom of the flexible member 102, the adhesive dressing then providing the generally flat bottom of the BNA 100 to be disposed upon a patient. As such, as used herein, the term "adhesive" will be understood and appreciated to encompass both a developed or applied layer of sticky material as well as a more traditional adhesive dressing as is used and known in the medical arts.

With respect to the exploded views of FIGS. 1E and 1F, the adhesive 114 has been shown as a distinct element, essentially a disc shaped adhesive dressing substantially conforming to the shape of the central region 104 of the flexible member 102. However, it will be understood and appreciated that depiction has been chosen for ease of illustration and discussion and to assist with appreciating the existence of the adhesive 114, but not as a limitation as a distinct element in all embodiments.

Returning most specifically to FIGS. 1A-1C, as shown, BNA 100 has a needle hub 118 disposed within the central region 104. The needle hub 118 receives a flexible tubing line 120 generally parallel to the generally flat bottom 110, and provides a needle 122 extending generally normal to the generally flat bottom 110 from the middle area 112 of the central region 104. As used herein, the term "flexible" as applied to the tubing 120 is understood and appreciated to mean that the tubing 120 is relatively pliable and will easily conform by bending and twisting by an operator. For at least one embodiment, the flexible tubing 120 has a luer connector structured and arranged for connection to a liquid source. Further still, for at least one embodiment the flexible tubing 120 is flow control tubing which may also be referred to as flow rate control tubing.

As will be further discussed and described below, the needle 122 is understood and appreciated to have a first length, and to be selected from a variety of different needle gauge options, such as, but not limited to, 24- to 30-gauge options. This first length will also be understood to be substantially the length of the needle protruding beyond the generally flat bottom 110.

As shown in FIG. 1A, a removable needle cover 124 is initially disposed about the needle 122, and this removable needle cover 124 is structured and arranged to removably engage with the needle hub 118. Moreover, for at least one embodiment, the removable needle cover 124 has a first end 126 which is structured and arranged to removably bind with the flexible member 102 and more specifically the needle hub 118. For at least one embodiment, the first end 126 provides opposing tabs 128 extending radially outward from the removable needle cover 124, which as shown in FIG. 1A, may be rotated to be disposed through side apertures 130 of the needle hub 118.

It will also be understood and appreciated that the removable needle cover 124 has an internal cavity space 132, which when initially engaged to the needle hub 118 provides a sealed space 132 about the needle 122. Further still, this sealed space 132 about the needle 122 may be a hermetically sealed space so as to ensure the needle is maintained in a sterile state until desired for use.

As is also shown in FIG. 1A-1F, BNA 100 also provides a closing system 134 structured and arranged to close the first side member 106 and the second side member 108 about the needle 122. For at least one embodiment, the closing system 134 is provided by a two-part system. More specifically, and as may be more fully appreciated with respect to FIG. 1B, for at least one embodiment, the closing system is provided at least in part by a button 136 disposed upon the generally flat bottom 110 proximate to a first distal edge 138 of the first side member 106 and a through hole 140 disposed proximate to a second distal edge 142 of the second side member 108.

Moreover, it will be appreciated that the first side member 106 extending away from the needle hub 118 is essentially a first butterfly wing 144 and the second side member 108 extending away from the needle hub 118 in opposition to the first butterfly wing 144 is essentially a second butterfly wing 146. It will be appreciated that the button 136 and the through hole 140 are disposed in substantially equal opposition relative to the needle hub 118, such that button 136 aligns to the through hole 140 when the first butterfly wing 144 and the second butterfly wing 146 are folded down and about the needle 122. It will also be understood and appreciated that the use of a button 136 and through hole 140 provides advantageous visual confirmation to the user that the first butterfly wing 144 and the second butterfly wing 146 are indeed secured about the needle 122—the user can see the button 136 protruding through the through hole 140. In addition, for at least one embodiment the geometry of the button 136 and through hole 140 may be dimensioned appropriately to provide an audible sound and tactile feedback when properly engaged.

As shown in FIG. 1B, it will be appreciated that for at least one embodiment, button 136 has at least one distal binding element 148, such as ridge 150. As the button 136 and/or through hole 140 are formed of compliant material, the distal binding element 148 of the button 136 may be compressed, and/or the through hole 140 permitted to expand, to permit the binding element 148 of the button 136 to press through the through hole 140. Once through, the button 136 and/or through hole 140 return to their substantially initial condition, the binding element 148 now disposed on the outside of the through hole 140, and thus binding the first butterfly wing 144 and the second butterfly wing 146 together.

Of course, it will be understood and appreciated that for at least one alternative embodiment, the orientation of the button 136 and the through hole 140 may be reversed, such that the button 136 is proximate to the second distal edge 142 and the through hole 140 is proximate to the first distal edge 138.

As may also be appreciated from at least FIGS. 1A & 1B, for at least one embodiment, flexible member 102 has a plurality of bend grooves 152 evenly disposed on either side of the needle hub 118 and normal to a long axis 154 running between the first distal edge 138 and the second distal edge 142. For the embodiment as shown in FIG. 1A, there are four bend grooves 152, two disposed in the first butterfly wing 144 and two disposed in the second butterfly wing 146, this number selected for ease of illustration and discussion, and not as a limitation. Moreover, it will be understood and appreciated that the number and arrangement of the bend grooves 152 may vary based on the patient demographics, and/or other design and fabrication issues without departure from the scope and teaching presented herein.

Although the flexible member 102 is indeed understood and appreciated to be flexible and capable of having the first butterfly wing 144 and second butterfly wing 146 bent downward for the closing system 134 to be engaged, the bend grooves 152 may further assist in such a bending process. Although the bend grooves 152 have been illustrated as disposed in the generally flat bottom 110, for at least one alternative embodiment one or more of the bend grooves 152 may be provided in the top surface 156 of BNA 100, the top surface 156 opposite from the generally flat bottom 110.

For at least one embodiment, BNA 100, and more specifically the needle hub 118 provides finger grippers 158 to assist a user in gripping and holding the BNA 100 as it is both placed upon a patient for treatment, and removed after treatment. For at least one embodiment, the finger grippers 158 are provided as extending ridges extending laterally from an upper portion of the needle hub 118. Nubs, bumps, ribs or other structures may also be provided in addition to, or as an alternative to, the extending ridges as finger grips 158.

As noted, the needle hub 118 receives a flexible tubing 120 generally parallel to the generally flat bottom 110, and provides a needle 122 extending generally normal to the generally flat bottom 110 from the middle area 112 of the central region 104. It will therefore be appreciated that there is essentially a 900 transition between the tubing 120 and the needle 122.

With respect to the exploded views of BNA 100 provided by FIGS. 1F and 1G, it will also be appreciated that for at least one embodiment, the needle hub 118 is provided by at least two elements—a needle hub frame 160 united with the flexible member 102 opposite from the generally flat bottom 110/adhesive 114, and a snap-in needle structure 162.

For at least one embodiment, the snap-in needle structure 162 is provided by a duct member 164 structured and arranged to join with the flexible tubing 120 at a first end 166 and to join with a needle 122 at a second end 168, the second end 168 generally normal to the first end 166. Moreover, as the duct member 164 achieves essentially about a 90° transition between the orientation of first end 166 as coupled to the tubing 120 and the second end 168 as coupled to needle 122, fabrication of BNA 100 may advantageously be performed with straight needles 122. As will be further discussed below, the duct member 164 is further structured and arranged for snap-in binding with the needle hub frame 160.

The exploded views of FIGS. 1F & 1G also provide a conceptual representation of the flexible tubing 120, which as noted above for at least one embodiment is flow control tubing. As is also shown, for at least one embodiment the tubing 120 is coupled to a luer 170 which may be connected to a liquid reservoir or other liquid source. For at least one embodiment, the luer 170 is a flared luer as set forth in U.S. Pat. No. 10,500,389 entitled, SYSTEM AND METHOD FOR FLARED LUER CONNECTOR FOR MEDICAL TUBING, incorporated herein by reference.

With respect to the present invention of BNA 100, it is understood and appreciated that the advantages herein described are achieved as a result of the combination of at least the flexible tubing element 120 and the snap-in needle 162 and their various flow rate characteristics when combined advantageously.

KORU Medical Systems, Inc. of Mahwah, New Jersey, is and has been a pioneer in needle set technology and flow rate control by means of specifically engineered flow control tubing. Indeed, KORU has realized that different flow rates may be provided by working with different flow combinations of flow control tubing, such as those systems and methods set forth in U.S. Pat. No. 10,420,886 entitled MULTI-FLOW UNIVERSAL TUBING SET, incorporated herein by reference, and U.S. Pat. No. 10,709,839 entitled PRECISION VARIABLE FLOW RATE INFUSION SYSTEM AND METHOD, incorporated herein by reference.

Further still, KORU has developed advantageous infusion systems permitting high flow at low pressure as set forth in U.S. application Ser. No. 17/729,914 published as US 2022/0265923 entitled HIGH FLOW AT LOW PRESSURE INFUSION SYSTEM, incorporated herein by reference. Moreover, varying embodiments of BNA 100 may incorporate pre-determined flow rates of flexible tubing 120, needle 122 and duct member 164, (and such other elements of the needle set comprising BNA 100) to provide one or more BNA's 100 as a single or multiple needle sets with pre-determined flow rates.

Figure 2A:
FIG. 2A is a front, upper perspective view of the flexible member of the butterfly needle assembly shown in FIGS. 1A-1F in accordance with at least one embodiment of the present invention.
Figure 2B:
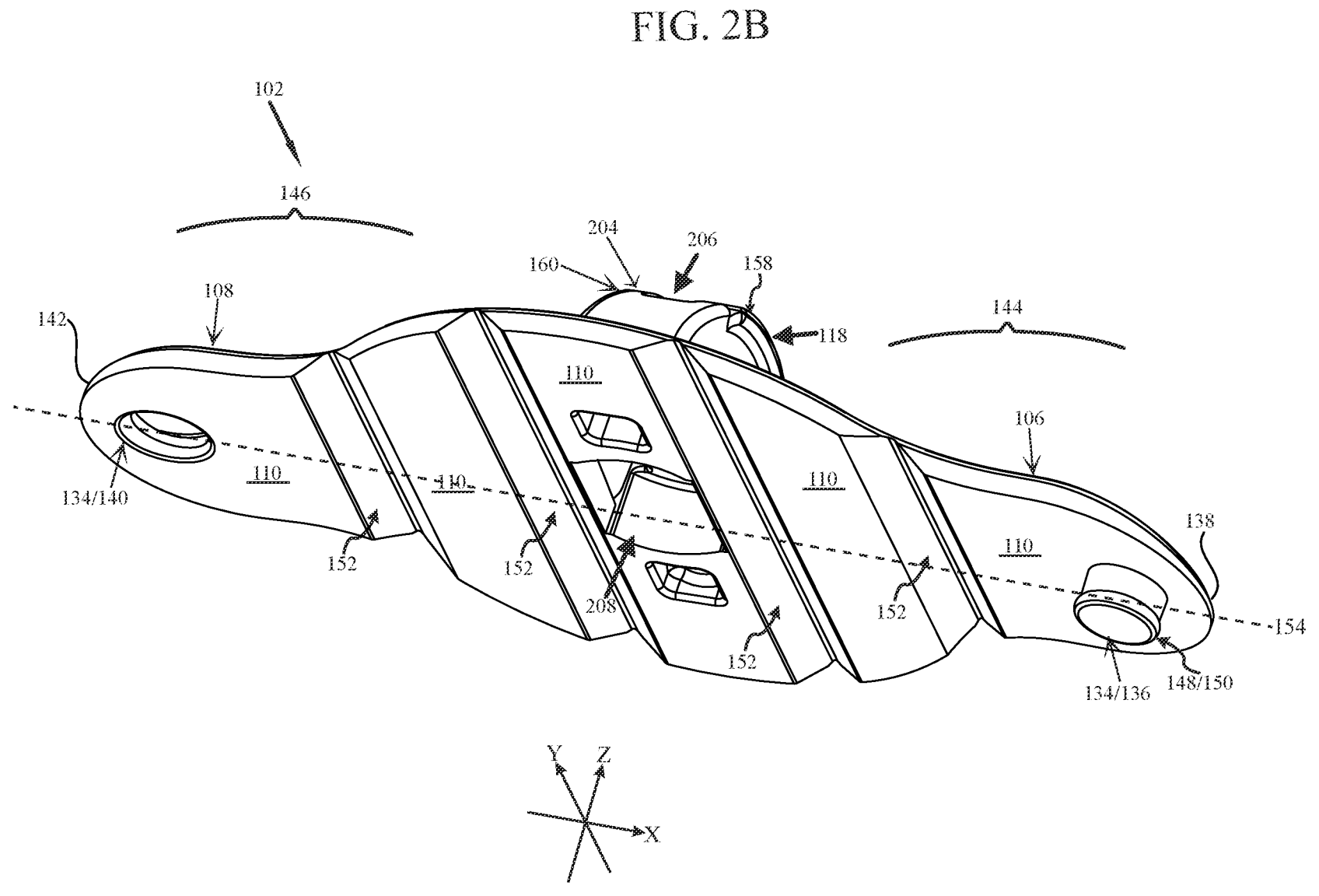

FIGS. 2A and 2B provide top and bottom perspective views of flexible member 102. For at least one embodiment the flexible member 102 is formed at least in part of medical grade flexible plastic, for example Polyethylene, Polypropylene, Thermoplastic Polyurethane (TPU), Polyvinyl Chloride (PVC), Silicone, or any other sustainable material. In varying embodiment, the flexible member 102 may be provided by casting, molding, stamping, and or 3D printing, and the flexibility of one area over another—such as the first butterfly wing 144 and the second butterfly wing 146 versus the needle hub frame 160 is do at least in part to the thickness of the material comprising the structure. The flexibility may also be adjusted by the use of different compounds or mixtures provided in one area verses another. Further still, puncture resistant material may be applied or disposed on or within portions of the first butterfly wing 144 and the second butterfly wing 146 as is further discussed below.

As may be appreciated in FIG. 2A depicting the top perspective, the needle hub frame 160 may be more fully appreciated. More specifically, at least one side aperture 130 may be appreciated clearly, which is structured and arranged to receive a side tab 128 provided by the first end 126 of the removable needle cover 124 (the tabs 128 and removable needle cover 124 not shown in FIG. 2A or 2B).

Indeed, stops 200 may be provided as elements of the apertures 130 against which the tabs 128 stop when the removable needle cover 124 is properly secured in place and temporarily bound to the flexible member 102. For at least one embodiment, stops 200 may be provided as thickened sections of material from which the needle hub frame 160 is established. For yet another embodiment, the stops 200 are formed of a harder or denser material which may be incorporated with the material providing the needle hub frame 160, or applied upon such material.

As may also be appreciated in FIG. 2A, for at least one embodiment, the lower portion 202 of the side apertures 130 is sloped upward towards stop 200. As such, when the tabs 128 of the removable needle cover 124 are rotated into place against stops 200, the sloped lower portion 202 will further drive and/or snuggly dispose the removable needle cover 124 in place. The geometry and dimensions of the tab 128 and sloped lower portion 202 are such that an axial force is provided to prevent the two components from separating.

Above the apertures 130 in the distal portion 204 of the needle hub frame 160, there is a first opening 206 which is structured and arranged to receive a snap-in needle structure 162 (not shown). The finger grips 158 may also be more fully appreciated on either side of first opening 206.

In FIG. 2B, the bend grooves 152 may be more fully appreciated as well, as is a second opening 208 from which the needle 122 will extend when the snap-in needle structure 162 is disposed in the first opening 206. This second opening 208 is also structured and arranged to receive the first end 126 of the removable needle cover 124. In FIG. 2B, the binding element 148, such as ridge 150 of the button 136 may also be more fully appreciated.

Figure 3A:
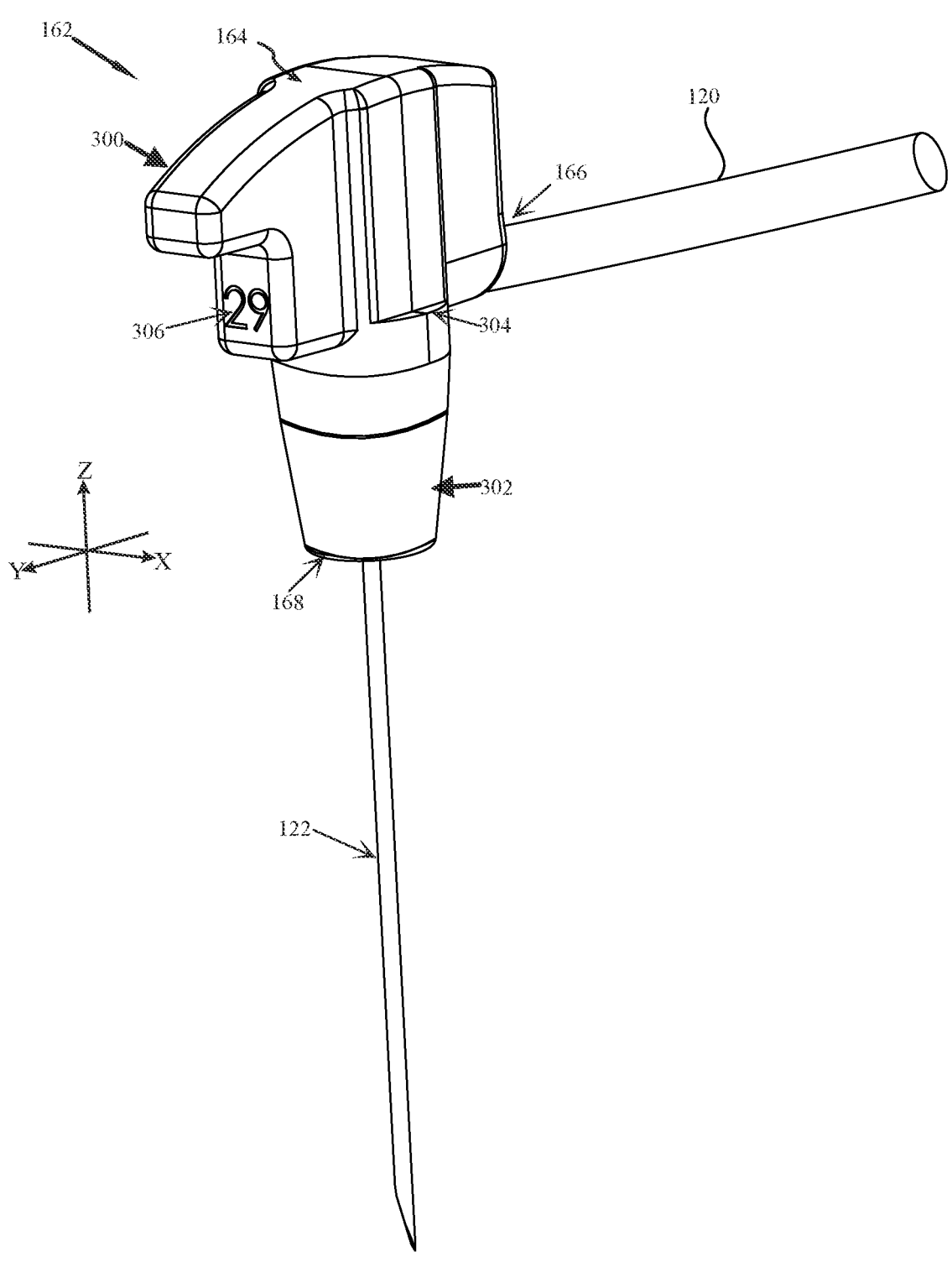
FIG. 3A is a front perspective view of a snap-in needle assembly to be disposed in the flexible member of the butterfly needle assembly in accordance with at least one embodiment of the present invention.
Figure 3B:
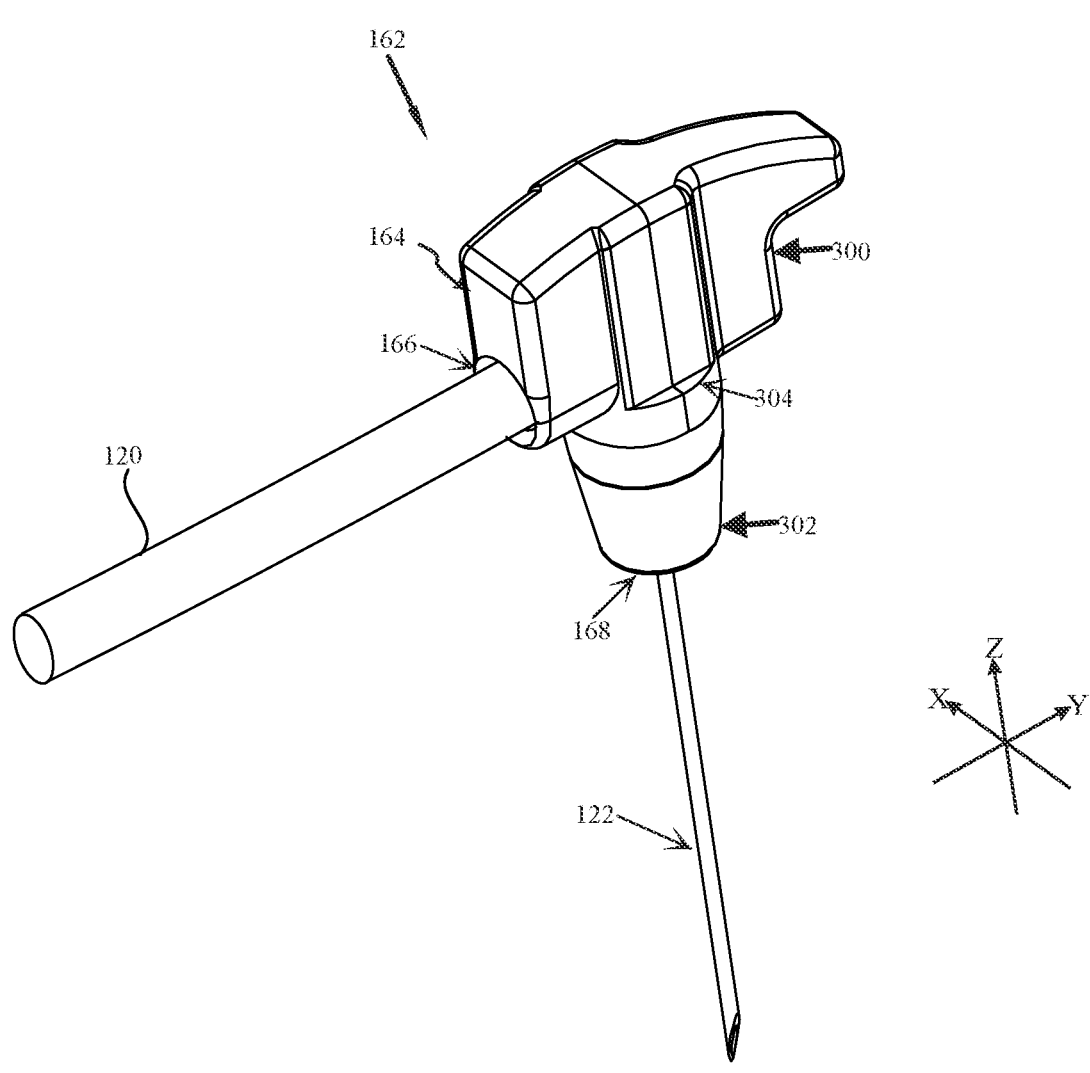
FIG. 3B is a rear perspective view of a snap-in needle assembly to be disposed in the flexible member of the butterfly needle assembly in accordance with at least one embodiment of the present invention.
Figure 3C:
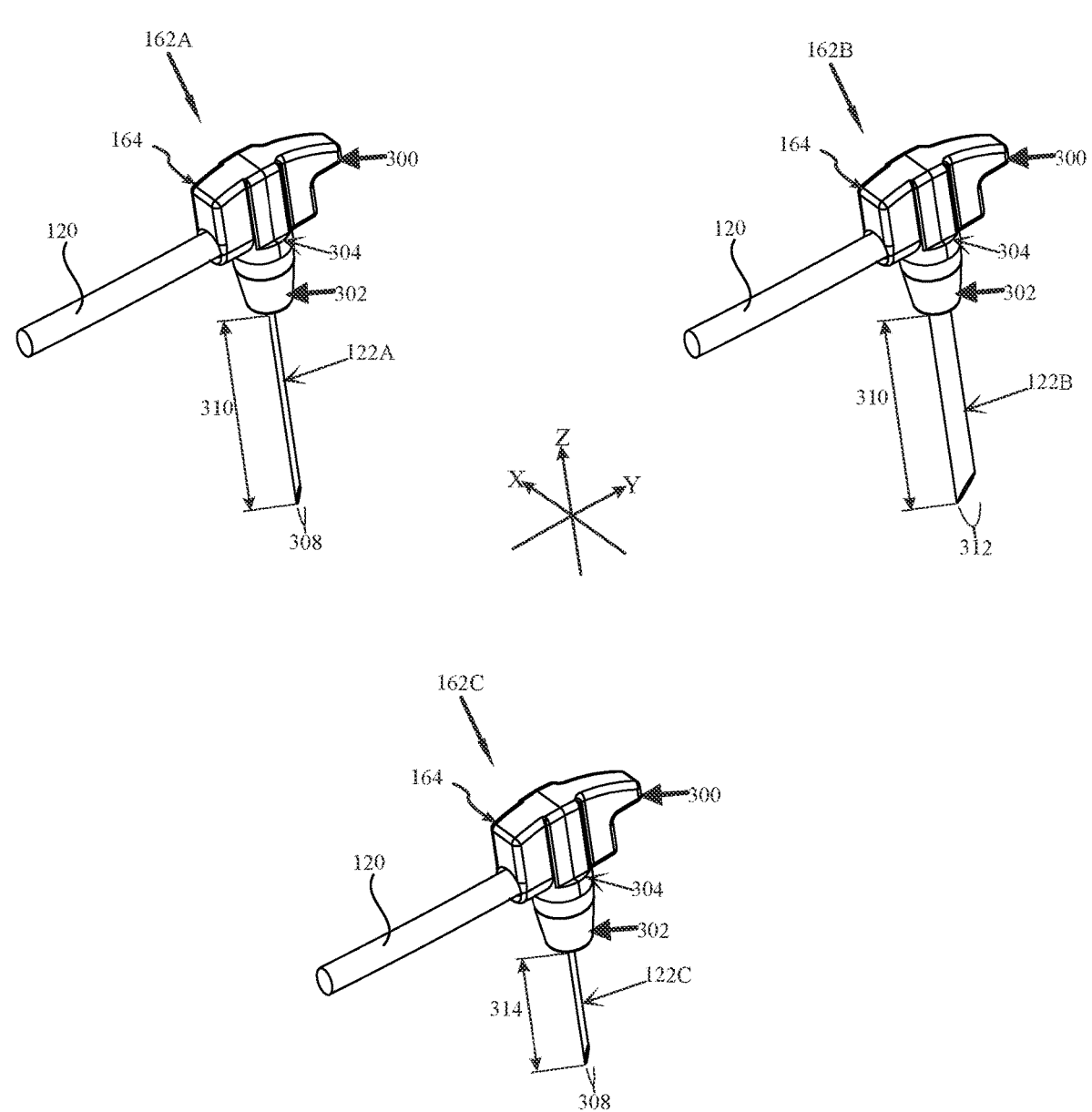
FIG. 3C presents three rear perspective views of different snap-in needle assemblies having different needles to be disposed in the flexible member of the butterfly needle assembly in accordance with at least one embodiment of the present invention.

FIGS. 3A-3C provide perspective front and rear views of the snap-in needle structure 162. As may be appreciated in FIGS. 3A and 3B, for at least one embodiment, the duct member 162 as an upper rectangular section 300 that receives the flexible tubing 120 and a lower conical section 302 that receives the needle 122. A ridge 304, or edge is provided at the transition between lower conical section 302 and the upper rectangular section 300. For at least one embodiment, this ridge is a binding surface that will mate with an internal and opposing ridge within the needle hub frame 160 when the snap-in needle structure 162 is fully disposed in the first opening 206 of the needle hub frame 160, which is more fully discussed below with respect to FIG. 4 providing a cut through of the flexible member 102, the needle hub frame 160 and the snap-in needle structure 162. As may also be appreciated in FIG. 3A, for at least one embodiment, the duct member 164 provides indicia 306 to indicate the gauge of the needle in the assembled snap-in needle structure 162.

As is shown in FIG. 3C, snap-in needle structures 162 may be provided having essentially the same duct member 164 but with distinctly different needles, e.g., needles 122A, 122B and 122C which advantageously permit three distinct snap-in needle structures 162A, 162B and 162C. More specifically, snap-in needle structure 162A conceptually illustrates a needle 122A with a first gauge 308 and a first length 310, snap-in needle structure 162B conceptually illustrates a needle 122B with a second gauge 312 that is distinctly different from the first gauge 308, and snap-in needle structure 162C conceptually illustrates a needle 122C having the first gauge 308 but a second length 314 that is distinctly different from the first length 310.

Moreover, a variety of different BNA's 100 may be quickly and easily fabricated simply by the selection of different snap-in needle structures 162, each of which is structured and arranged to snap fit in the first opening 206 of the needle hub frame 160 provided by the flexible member 102.

Figure 4:
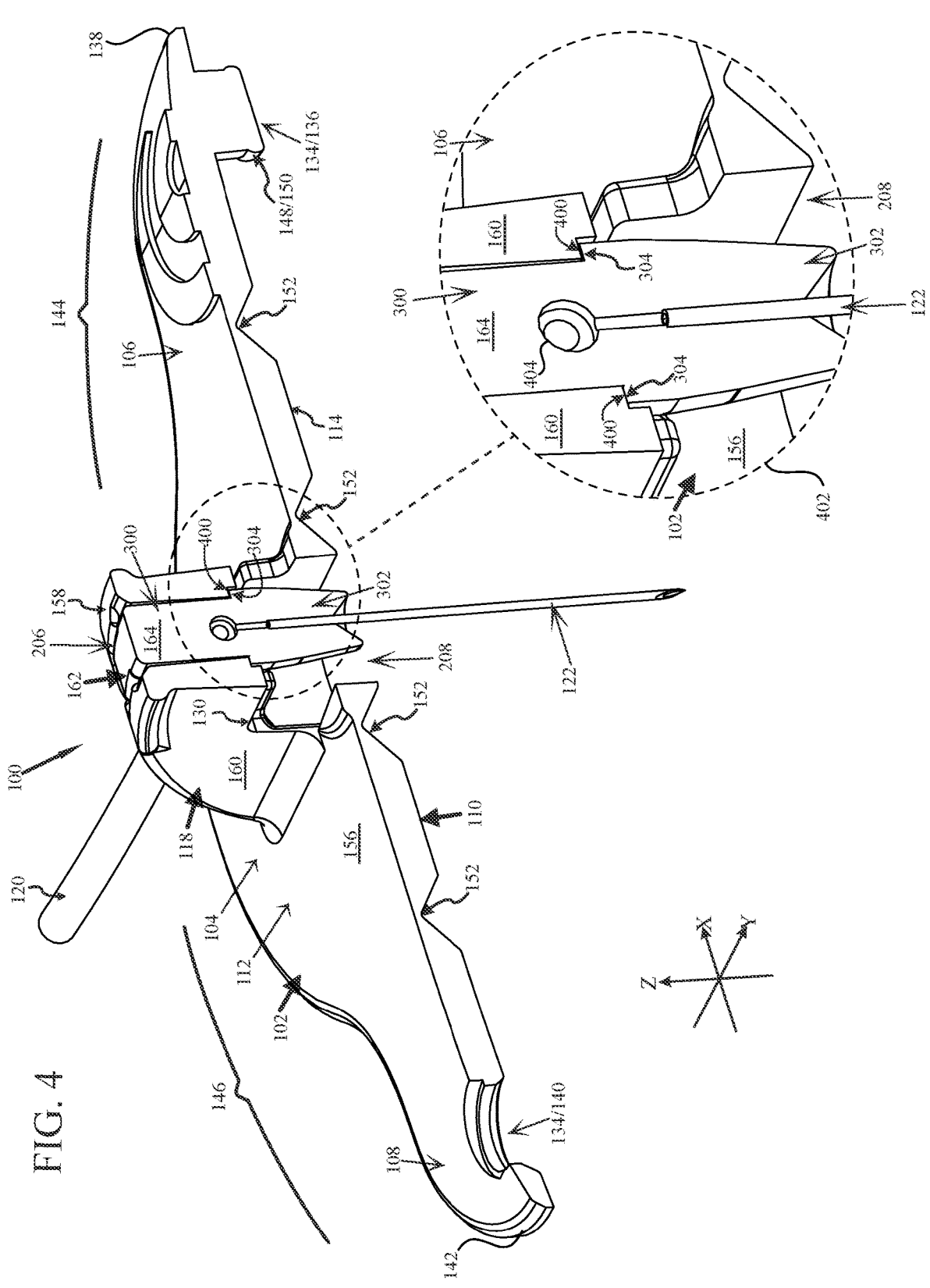
FIG. 4 is a front perspective, cut through view of a butterfly needle assembly further depicting the snap-in function of disposing the snap-in needle assembly into the flexible member to provide a butterfly needle assembly in accordance with at least one embodiment of the present invention.

Turning to FIG. 4, provided is a cross section perspective view of BNA 100, and most specifically a cut-through of flexible member 102, needle hub frame 160 and snap-in needle structure 162 as fully disposed in the first opening 206 to appreciate the nature of the snap-in binding. More specifically, and as may be more fully appreciated in enlarged oval 402, ridge 304 of the snap-in needle structure 162 is shown engaging with and below ridge 400 of the needle hub frame 160 such that the snap-in needle structure 162 is now in a binding attachment with the needle hub frame 160.

Moreover, as the snap-in needle structure 162 is disposed down into first opening 206, the lower conical section 302 will cause deflection of the needle hub frame 160 outward. When the conical section 302 has passed beyond ridge 400 the outward deflection ceases and the resilient material providing the needle hub frame 160 returns to its original state, and thus ridge 400 of the needle hub frame is disposed over ridge 304 of the snap-in needle structure 162.

FIG. 4 also permits the internal channel 404 that is structured and arranged within the duct member 162 to fluidly interconnect and transition liquid received from the tubing 120 to the needle 122. It will be understood and appreciated that, for at least one embodiment, the internal channel 404 is structured and arranged to smoothly transition the direction of liquid flow, such as by providing smooth sloping walls to minimize eddy currents and fluid turbulence. Moreover, as noted in U.S. application Ser. No. 17/729,914 identified above, for at least one embodiment, the infusion system incorporating BNA 100 is structured and arranged to substantially maintain laminar flow of the liquid through the tubing 120, the duct member 164 and needle 122 for high flow rate delivery of the liquid into the patient at low pressure.

Figure 5A:
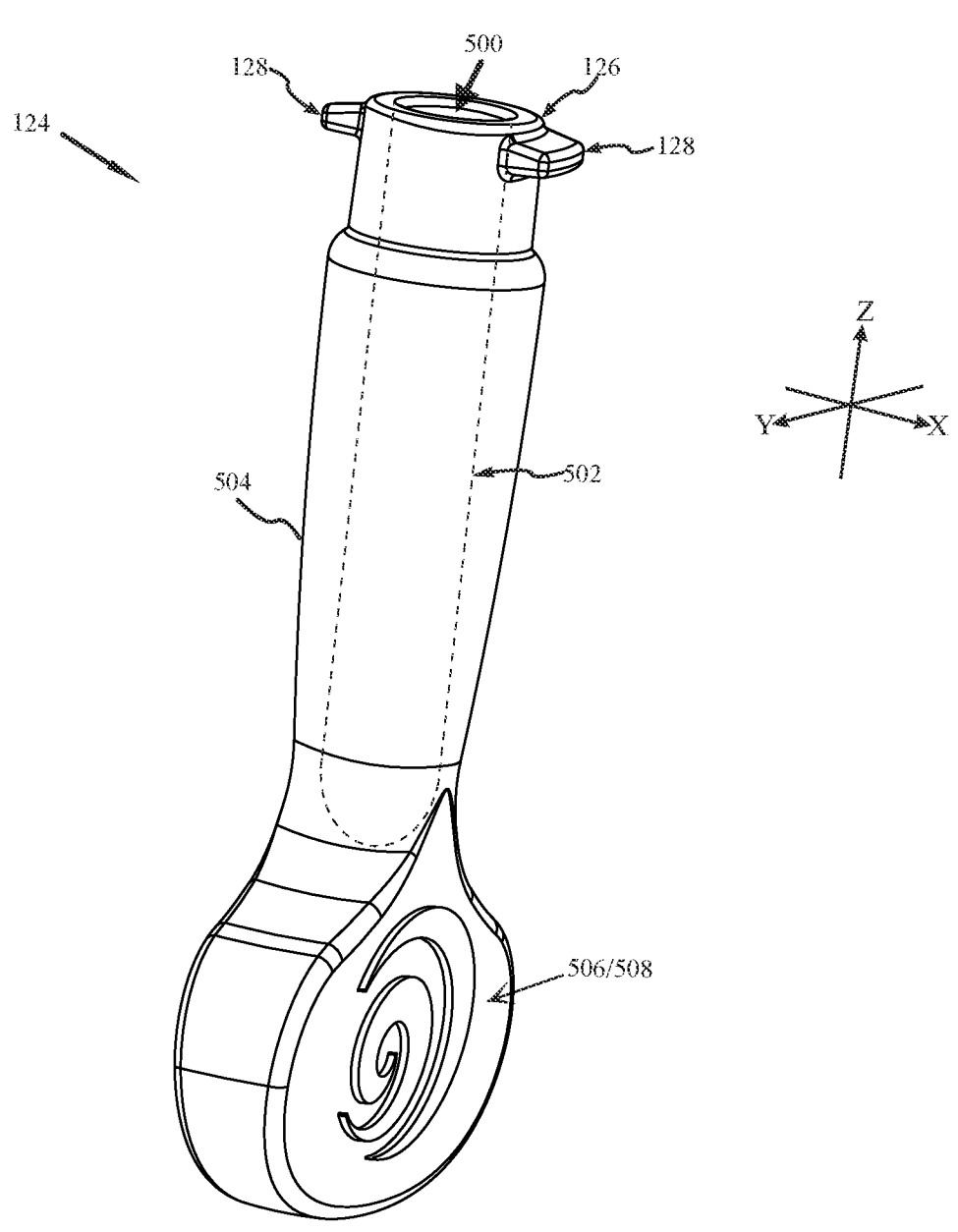
FIG. 5A is a front perspective view of the removable needle cover shown in FIG. 1A in accordance with at least one embodiment of the present invention.
Figures 5B, 5C, 5D:
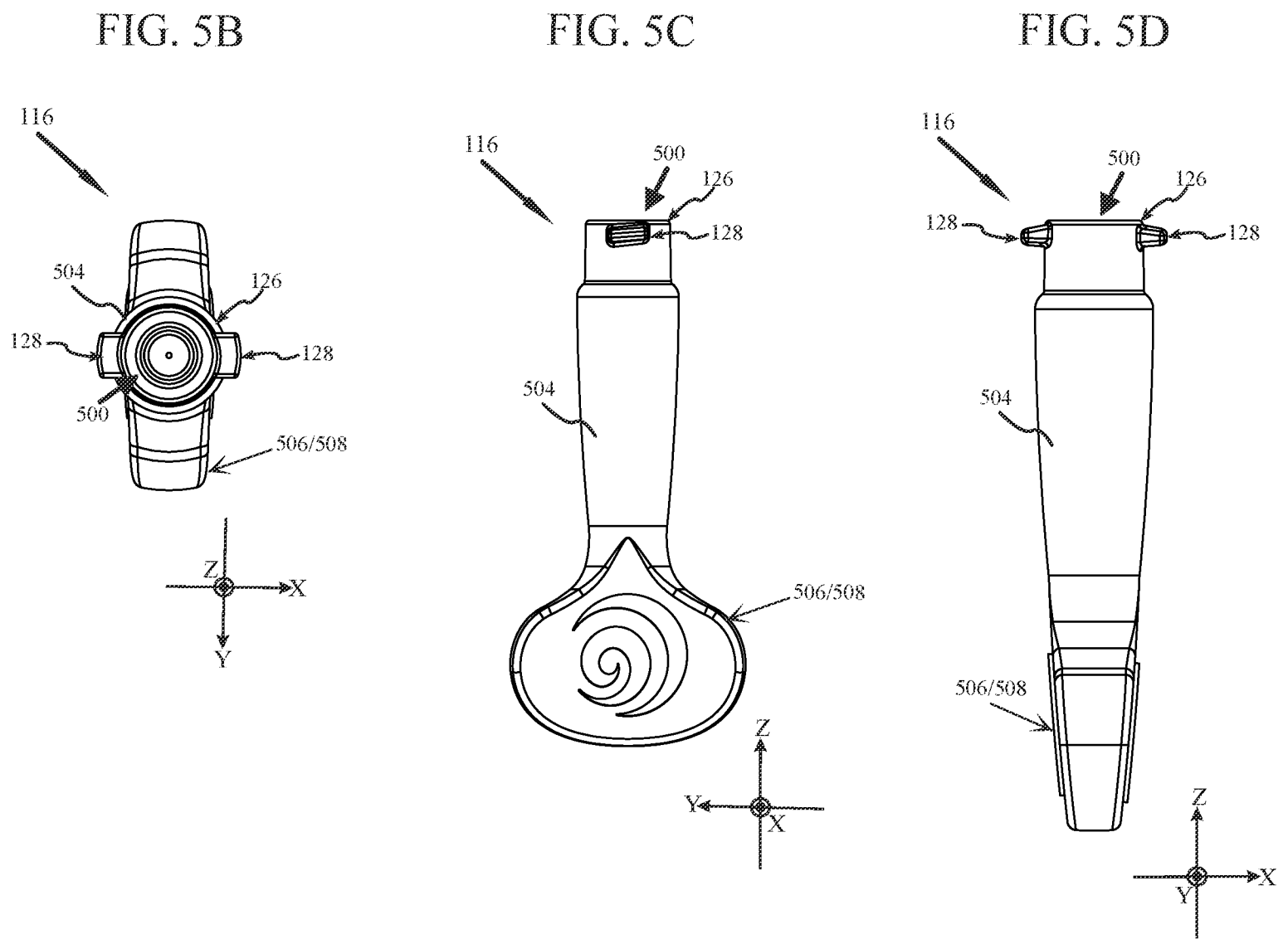

FIGS. 5A-5D present the removable needle cover 124, first in perspective (See FIG. 5A), and then in following top plane view (FIG. 5B), side plane view (FIG. 5C) and front plane view (FIG. 5D).

With respect to FIGS. 5A-5D the side tabs 128 may be more fully appreciated. With specific respect to FIG. 5C, it may also be appreciated that for at least one embodiment the tabs 128 are angled to align with the sloped lower portion 202 of the first apertures of the needle hub frame 160 (not shown in FIGS. 5A-5D, see FIG. 2A).

In addition, it will be appreciated that the first end 126 of the removable needle cover 124 provides an opening 500 to an internal hollow chamber 502 within the body 504 of removable needle cover 124. Opening 500 is structured and arranged to engage with the lower conical section 302 of the snap-in needle structure 162. More specifically, as the removable needle cover 124 is disposed through the second opening 208 of the flexible member 102 and twisted so as to drive the tabs 128 to rotatably lock into the needle hub 118, the opening 500 is press fit about at least a portion of the lower conical section 302 so as to provide a substantially airtight seal between the removable needle cover 124 and the lower conical section 302 of the snap-in needle structure 162.

It is this air tight seal that achieves the sealed space 132 as noted above about the needle 122 in the assembled BNA 100. For at least one embodiment, at least a portion of the material defining the opening 500 may be a soft, and/or elastic or pliable material so as to further facilitate the formation of an air tight seal with the lower conical section 302 of the snap-in needle structure 162.

As is also shown in FIGS. 5A-5D, for at least one embodiment, the removable needle cover 124 provides a grip 506, such as enlarged knob 508 to facilitate installing and removing the removable needle cover 124 from the needle hub 118.

Figure 6A:
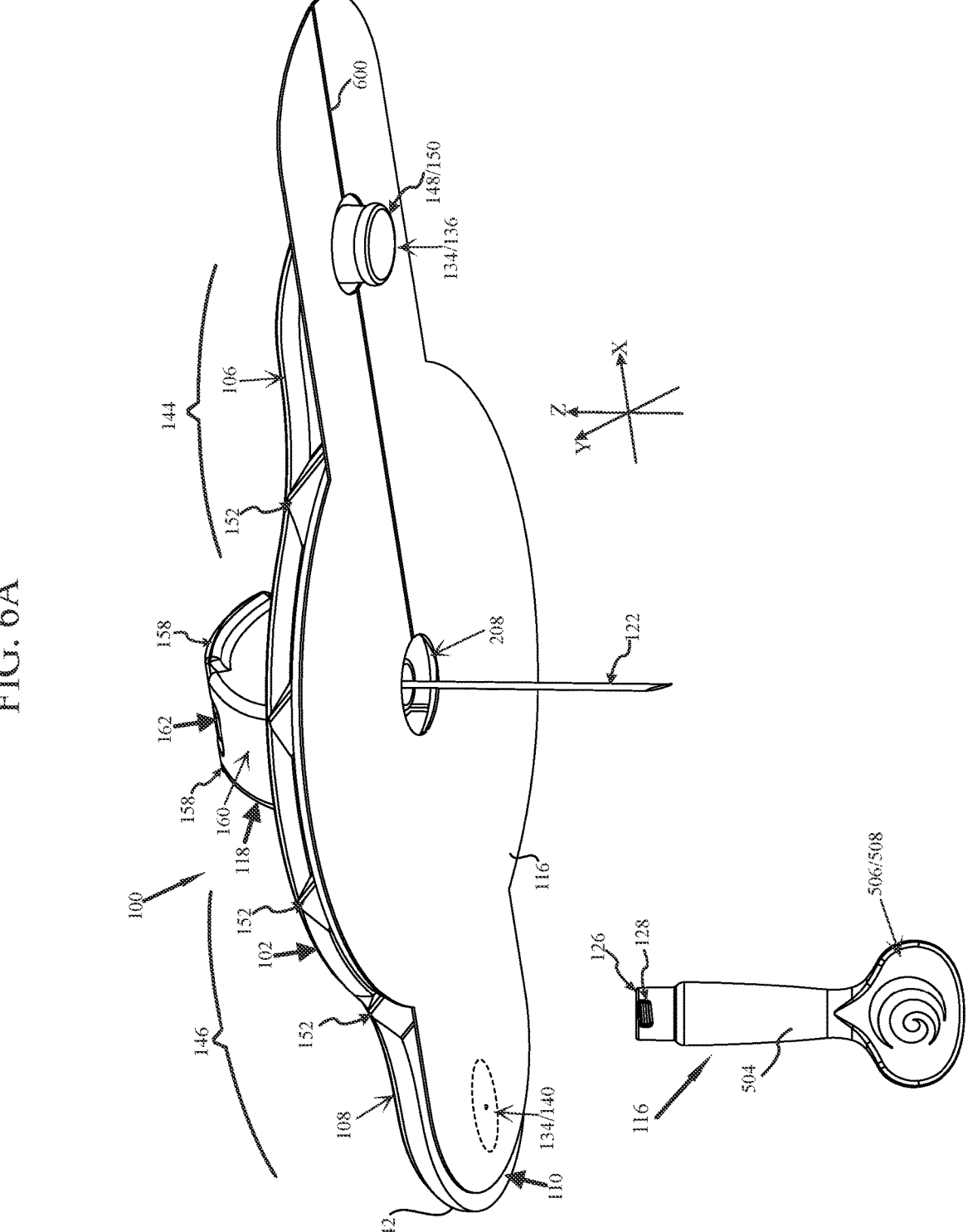
FIG. 6A is a front lower perspective view of a butterfly needle assembly with the removable needle cover now removed in accordance with at least one embodiment of the present invention.

FIG. 6A presents bottom perspective view of BNA 100 wherein the removable needle cover 124 has been removed, such that needle 122 is now exposed. With the removable needle cover 124, the removable cover 116 protecting the adhesive may now also be easily removed, and for at least one embodiment the removable cover 116 has a pre-defined tear line 600 which may assist the user in easily, and fully removing the removable cover 116 so as to expose the adhesive.

Figure 6B:
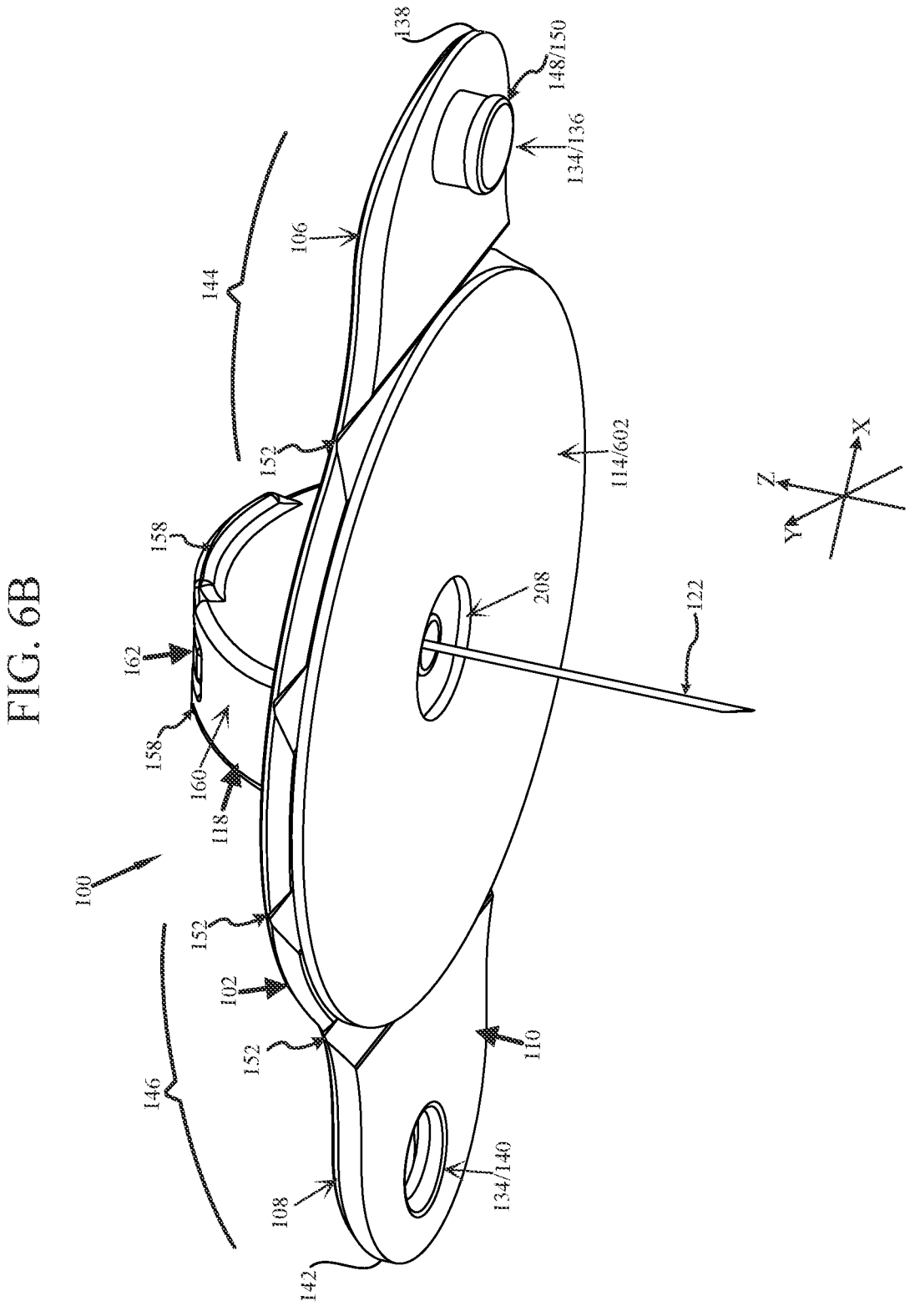
FIG. 6B is a front lower perspective view of an embodiment of the butterfly needle assembly with the removable cover removed to expose the adhesive as a distinct layer in accordance with at least one embodiment of the present invention.
Figure 6C:
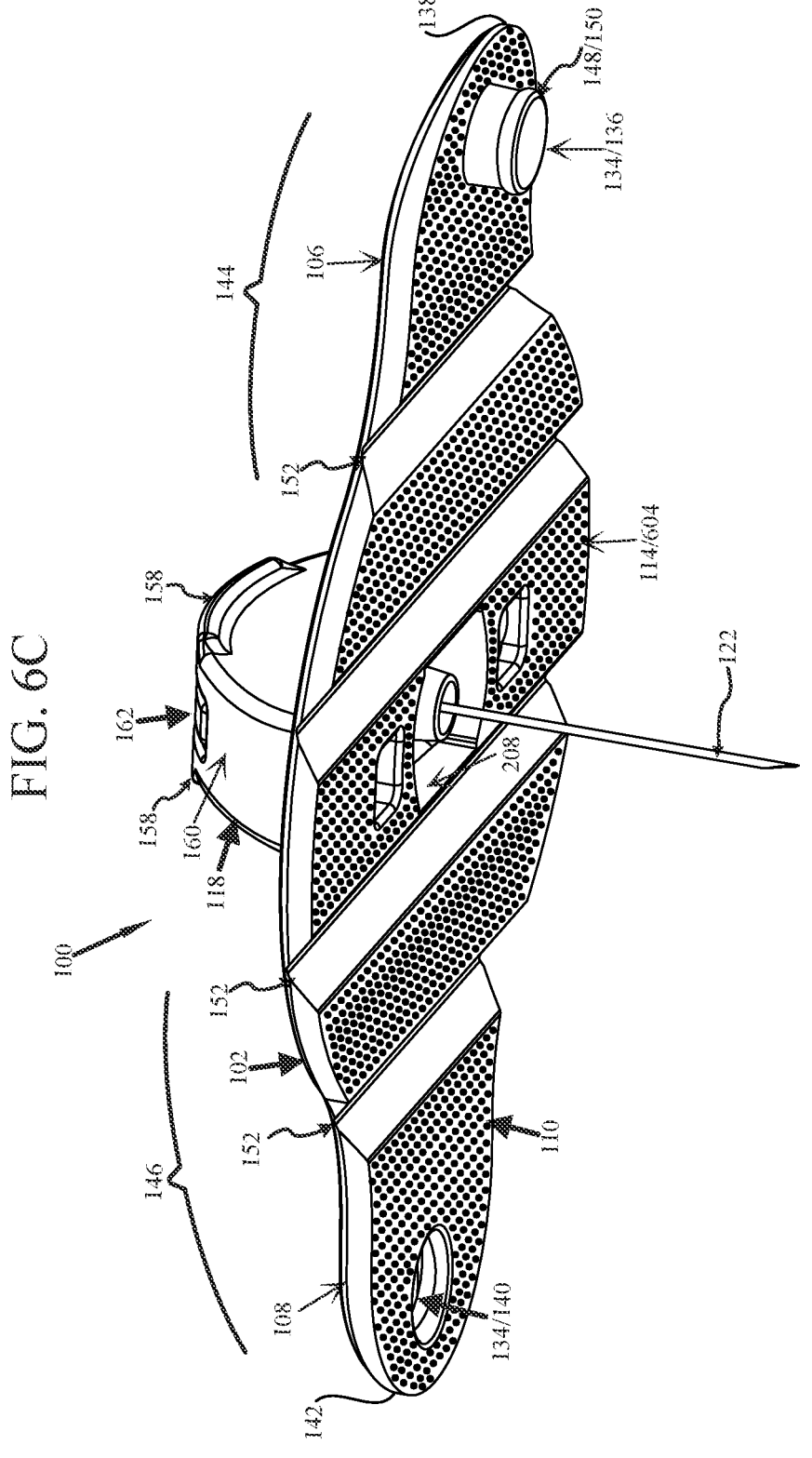
FIG. 6C is a front lower perspective view of another embodiment of the butterfly needle assembly with the removable cover removed to expose the adhesive as an incorporated element of the generally flat bottom of the flexible member in accordance with at least one embodiment of the present invention.

FIGS. 6B and 6C provided substantially the similar embodiments of BNA 100, with the embodiment of BNA 100 shown in FIG. 6B having an adhesive 114 as a distinct pad 602 or layer of material, that as with flexible member 102 is highly flexible and able to conform to the contours of the body of the patient upon which BNA 100 will be disposed for an infusion treatment, as well as to permit the first butterfly wing 144 and second butterfly wing 146 to be folded down and about the needle 122 after use so as to protect from accidental needle stick. As shown, for at least one embedment, the adhesive pad 602 is provided as a generally circular or elliptic element that is confirming to the primary portion of the bottom of the flexible member 102, but leaving the closing system 134 unincumbered. Of course, for at least one alternative embodiment, the adhesive pad 602 may conform to essentially all of the bottom of the flexible member 102, including about the elements of the closing system.

FIG. 6C provides a substantially similar view of BNA 100 as in FIG. 6B, however, here the adhesive 114 has been established by spray, dip, roll-on, or other application process such that it may be considered an element of the generally flat bottom 110 itself, represented as dots 604. Moreover, for the embodiment of FIG. 6C, the adhesive 114/604 may be described as similar to that of a traditional adhesive bandage, whereas in FIG. 6B, the adhesive 114/602 is an additional layer which may provide additional softening/comforting to the patient, and for at least one embodiment may also provide a limited absorptive property should the infusion sight weep or blead.

Figure 7A:
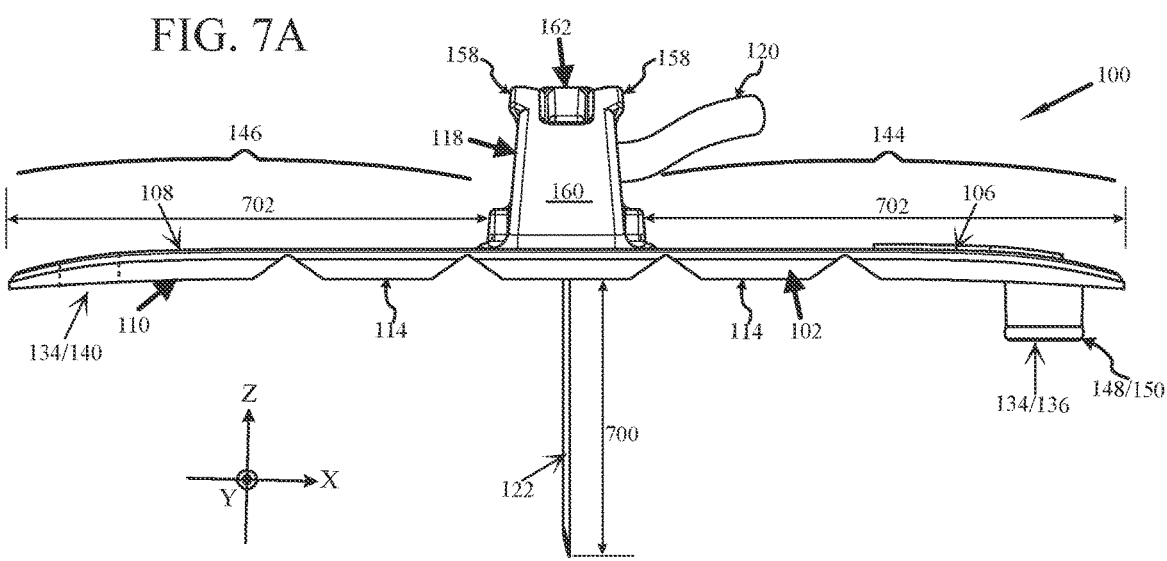
FIG. 7A is a front plane view of the butterfly needle assembly with needle exposed prior to the closing system being engaged about the needle in accordance with at least one embodiment of the present invention.

FIGS. 7A-7D present side plane view of BNA 100 so as to further appreciate the advantageous closing system 134 in accordance with at least one embodiment. Moreover, FIG. 7A presents an initial side plane view of BNA 100 permitting an appreciation for the relationship of the first and second butterfly wings 144 & 146 and the needle 122.

More specifically, as shown in FIG. 7A, the needle has a first length 700 extending below the generally flat bottom 110. The first side member 106, aka first butterfly wing 144, and the second side member 108, aka second butterfly wing 146, have substantially the same second length 702 from the central region 104, and as is shown in FIG. 7A the second length 702 is greater than the first length 700. As such, when the first and second butterfly wings 144 & 146 are folded down about the needle 122, the first and second butterfly wings 144 & 146 will completely enclose the distal end of needle 122.

Figure 7B:
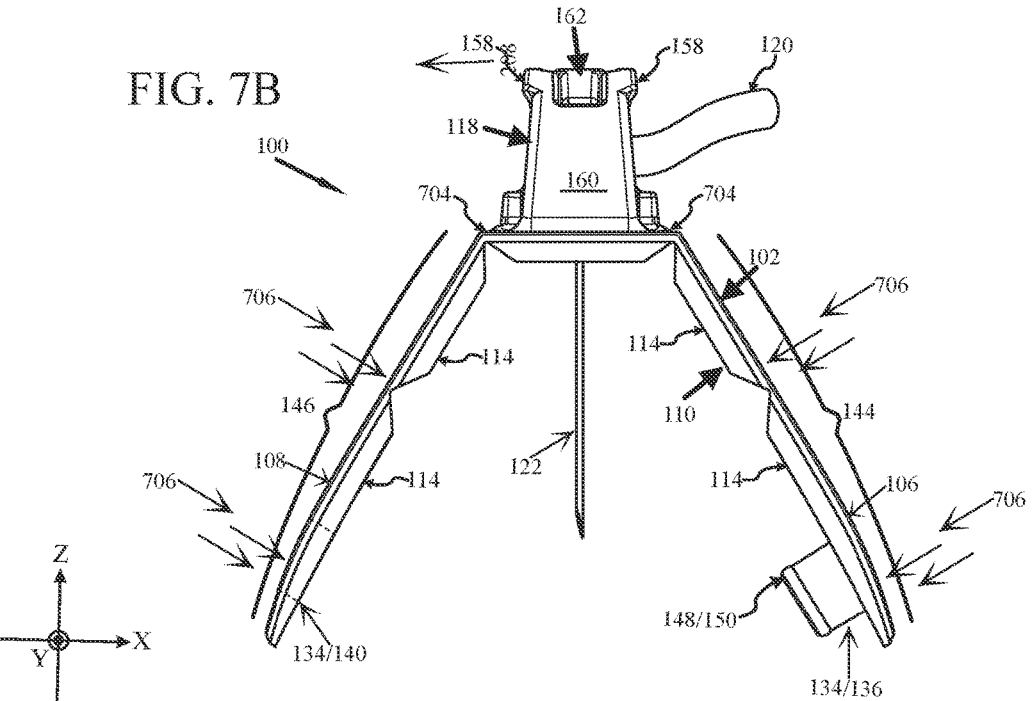
FIG. 7B is a front plane view showing the progression from FIG. 7A of the butterfly needle assembly as the wings are bent down to enclose the needle in accordance with at least one embodiment of the present invention.

FIG. 7B presents an initial folding of the first and second butterfly wings 144 & 146 downward so as to eventually enclose the needle 122. As noted above, flexible member 102 is intended to be made substantially of a flexible material. However, as the needle hub 118 is an integrated component of the flexible member 102, and as such provides a thicker area of material, for at least one embodiment, the folding of the first and second butterfly wings 144 & 146 will most easily be initiated along the sides 704 of the needle hub 118 as force (shown by arrows 706) is applied to the first and second butterfly wings 144 & 146.

For at least one embodiment, as the first and second butterfly wings 144 & 146 close, the flexible nature of the flexible member 102, and more specifically the flexibility of the first and second butterfly wings 144 & 146 advantageously permits the them to more completely enclose the needle 122, then would be achieved if the first and second wings were more ridged structures.

Figure 7C:
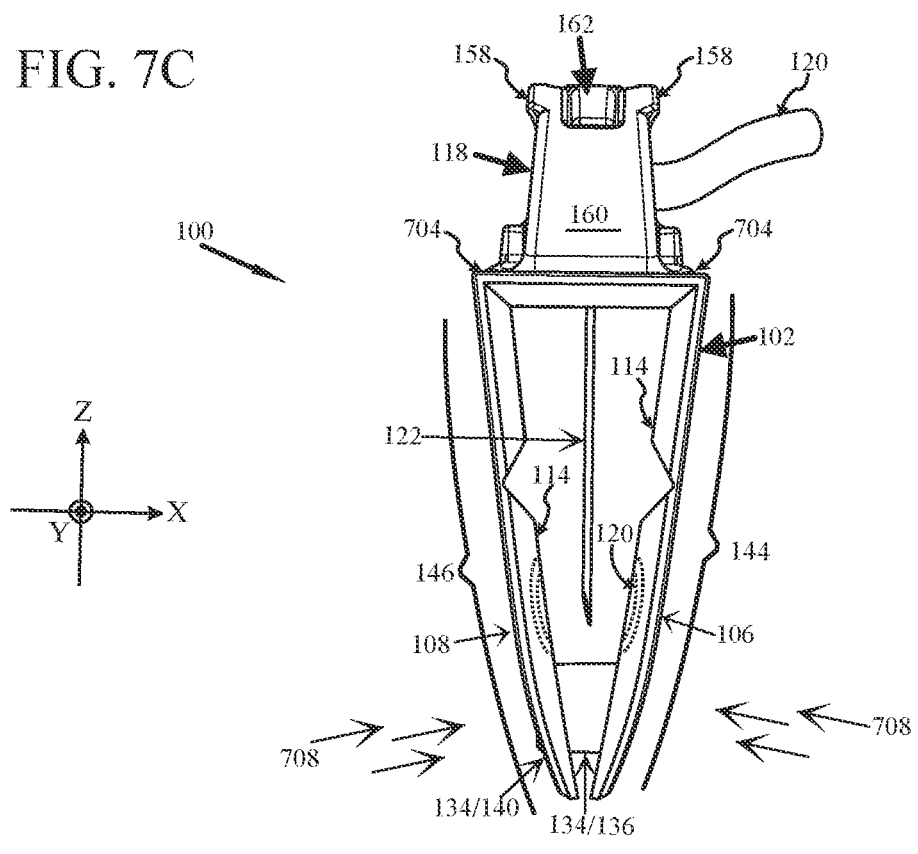
FIG. 7C is a front plane view showing the progression from FIG. 7B as the closing system is at least partially engaged to enclose the needle in accordance with at least one embodiment of the present invention.

Indeed, as is shown in FIG. 7C, as the first and second butterfly wings 144 & 146 are further bent downward, the closing system 134 begins to engage, as force (shown as arrows 708) is applied towards the distal end For at least one embodiment, as noted above, this closing system is provided at least in part by button 136 and through hole 140. As is shown in FIG. 7C the button 136 is now disposed at least partially into through hole 140, if not partially therethrough.

Figure 7D:
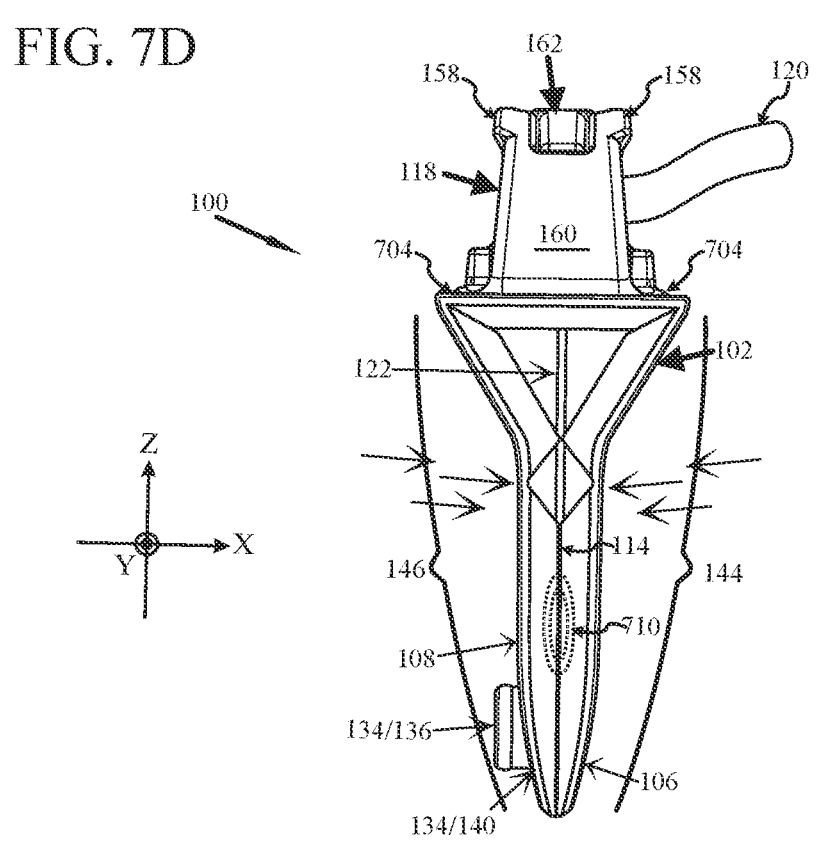
FIG. 7D is a front plane view showing the progression from FIG. 7C as the closing system is fully engaged and portions of the wings are pressed together to enclose the needle in accordance with at least one embodiment of the present invention.

While this may indeed substantially enclose needle 122, an even more advantageous close state is achieved for at least one embodiment by a person simply pressing the first and second butterfly wings 144 & 146 together as shown in FIG. 7D. In addition, as is first shown in FIG. 7C, for at least one embodiment, at least a portion of the first and second butterfly wings 144 & 146 may include cut resistant/puncture resistant material 710 (shown in dotted relief) so as to substantially reduce the chance of an accidental needle stick should the first and second butterfly wings 144 & 146 be further bent about the needle.

Moreover, as may be appreciated in FIG. 7D, the adhesive 114 which previously assisted in anchoring the BNA 100 to the patient's skin, now binds the first and second butterfly wings 144 & 146 together in physical contact about at least a portion of the needle 122, and most importantly about the sharp end of the needle. In this final state, the opportunity for an accidental needle stick from a used BNA 100 is significantly reduced as the first and second butterfly wings 144 & 146 and mechanically fastened and adhesively stuck together. And further still, for at least one embodiment it may also be appreciated that the cut resistant/puncture resistant material 710 of the first and second butterfly wings 144 & 146 is substantially about the location of the needle tip within the now sealed BNA 100.

To summarize the above descriptions, for at least one embodiment, the present invention provides a BNA 100, including: a flexible member 102 having a central region 104 with a first side member 106 and a second side member 108 collectively providing a generally flat bottom 110, the central region 104 having a middle area 112; an adhesive 114 dressing disposed upon the generally flat bottom 110, the adhesive 114 dressing protected by a removable cover 116; a needle hub 118 disposed within the central region 104, the needle hub 118 receiving a flexible tubing 120 line generally parallel to the generally flat bottom 110 and providing a needle 122 extending generally normal to the generally flat bottom 110 from the middle area 112 of the central region 104, the needle 122 extending for a first length; a removable needle cover 124 initially disposed about the needle 122, the removable needle cover 124 structured and arranged to removably engage with the needle hub 118; and a closing system 134 structured and arranged to close the first side member 106 and the second side member 108 of the flexible member 102 about the needle 122.

For yet another embodiment, the present invention provides a BNA 100, including: a flexible member 102 having a central region 104 with a first side member 106 and a second side member 108 collectively providing a generally flat bottom 110; an adhesive 114 dressing disposed upon the generally flat bottom 110, the adhesive 114 dressing protected by a removable cover 116; a needle 122 hub frame 160 united with the flexible member 102 opposite from the adhesive 114 dressing; a snap-in needle structure 162 provided by a duct member 164 having a first end 166 and a second end 168, the first end 166 joined with a flexible tubing 120 line and the second end 168 joined with a needle 122 having a first length, the second end 168 generally normal to the first end 166, the duct member 164 further structured and arranged for snap-in binding with the needle hub frame 160, the needle 122 extending generally normal to the generally flat bottom 110 from a middle area 112 of the central region 104, the flexible tubing 120 generally parallel to the generally flat bottom 110 proximate to the first end 166 of the duct member 164; and a removable needle cover 124 initially disposed about the needle 122, the removable needle cover 124 structured and arranged to removably engage with the needle hub frame 160; and a closing system 134 structured and arranged to close the first side member 106 and the second side member 108 of the flexible member 102 about the needle 122.

A method of providing at least one embodiment of BNA 100 as described above may be provided by providing a flexible member 102 having a central region 104 with a first side member 106 and a second side member 108 collectively providing a generally flat bottom 110, the central region 104 having a middle area 112; providing an adhesive 114 dressing upon the generally flat bottom 110, the adhesive 114 dressing protected by a removable cover 116. The method continues with providing a needle hub 118 disposed within the central region 104, the needle hub 118 receiving a flexible tubing 120 line generally parallel to the generally flat bottom 110 and providing a needle 122 extending generally normal to the generally flat bottom 110 from the middle area 112 of the central region 104, the needle 122 extending for a first length. As has been described above, for at least one embodiment the needle hub 118 may be provided as a needle hub frame 160 an selecting a specific snap-in needle structure 162 which is snap-fit into the needle hub frame 160. The method further includes providing a removable needle cover 124 initially disposed about the needle 122, the removable needle cover 124 structured and arranged to removably engage with the needle hub 118; and providing a closing system 134 structured and arranged to close the first side member 106 and the second side member 108 of the flexible member 102 about the needle 122.

Having described several physical embodiments of BNA 100, it will be further appreciated that for at least one embodiment, the flexible tubing 120, duct member 164 and needle 122 may be joined as an inseparable assembly through the use of Ultraviolet (UV) curable glue, medical grade cyanoacrylate glue, or other suitable bonding agents.

Figures 8, 9:
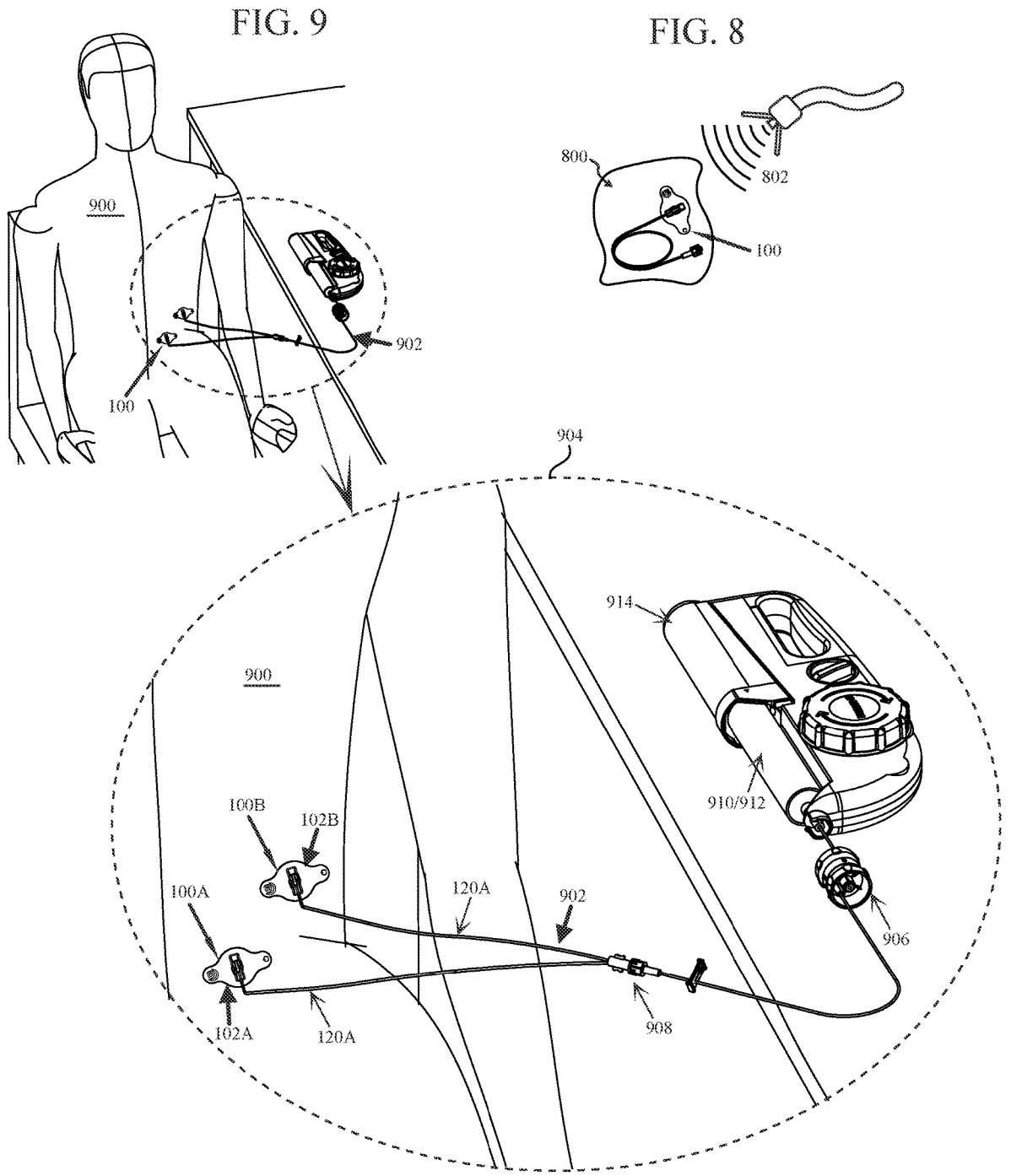
FIG. 8 presents a conceptual illustration of an assembled butterfly needle assembly in packaging being sterilized in accordance with at least one embodiment of the present invention.
FIG. 9 presents a conceptual illustration of an infusion procedure utilizing at least one butterfly needle assembly in accordance with at least one embodiment of the present invention.

To further appreciate the advantageous use of BNA 100, FIG. 8 presents a conceptual illustration of an assembled BNA 100 disposed in appropriate packaging 800, which in turn is sterilized by the application of radiation 802. As the removable needle cover 124 is disposed about the needle 122 and therefor establishes the sealed space 132 as discussed above, the sterilization process ensures that the needle is sterilized and will remain sterilized until the removable needle cover 124 is removed prior to inserting BNA 100 into a patient.

FIG. 9 presents a conceptualized infusion session for a patient 900. More specifically, a needle set 902 incorporating two BNAs 100 (e.g., BNA 100A and BNA 100B) has been disposed into a patient 900 in the lower torso area. As BNAs 100A and 100B have the advantageous adhesive 114 on the generally flat bottom 110, no further tape is required.

As may be more fully appreciated in enlarged oval section 904, the needle set 902 is connected to a flow controller 906—this connection may be through a luer 908, or optionally the flow controller 906 may be provided as an established and inseparable element of the needle set 902. Needle set 902 is in turn connected to a liquid source or reservoir 910, such as a syringe 912.

For at least one embodiment, it is understood and appreciated that the needle set 902 is advantageously structured and arranged for use with a constant pressure pump 914, such as the Freedom60® Syringe Infusion Pump or the FreedomEdge Syringe Infusion Pump as provided by KORU Medical Systems, Inc. of Mawah, New Jersey. Constant pressure systems, such as constant pressure pump 914, when combined with BNA 100, and more specifically needle sets such as needle set 902 may be highly advantageous in preventing unintended and/or unsafe rates of administration of the liquid from the liquid reservoir 910 to the patient 900.

With a constant flow rate system, the pressure is increased in response to any flow restriction no matter if such a restriction is the build-up of pressure in the patient's tissues or an element of the delivery system. This can result in an administration of the liquid at an unsafe pressure. As such, the patient may suffer a wide range of symptoms, including, but not limited to, vein collapse, anaphylaxis, overdose, histamine reactions, morbidity, and mortality.

Although BNA 100 is intended for placement upon an infusion patient by hand, needle insertion devices are often used. Accordingly, it will be understood and appreciated that varying embodiments of BNA 100 may be provided in which the needle hub 118, and more specifically the needle hub frame 160 and/or the apertures 130 are structured and arranged for engagement by embodiments of needle insertion devices taught by U.S. Pat. No. 10,478,569 entitled NEEDLE INSERTION DEVICE, incorporated herein by reference, U.S. Pat. No. 10,559,635 entitled NEEDLE INSERTION DEVICE, incorporated herein by reference, and U.S. patent application Ser. No. 18/071,775 entitled NEEDLE INSERTION DEVICE, incorporated herein by reference. Moreover, at least one embodiment of BNA 100 has an appropriate geometry of, but not limited to, the flexible member 102 and/or the needle hub 118 and/or the side apertures 130, to be engaged by one or more of the needle insertion devices provided by KORU Medical Systems, Inc. of Mawah, New Jersey.

Changes may be made in the above methods, systems and structures without departing from the scope hereof. It should thus be noted that the matter contained in the above description and/or shown in the accompanying drawings should be interpreted as illustrative and not in a limiting sense. Indeed, many other embodiments are feasible and possible, as will be evident to one of ordinary skill in the art. The claims that follow are not limited by or to the embodiments discussed herein, but are limited solely by their terms and the Doctrine of Equivalents.

What is claimed:

1. A butterfly needle assembly, comprising:
  a flexible member having a central region with a first side member and a second side member collectively providing a generally flat bottom, the central region having a middle area;
  an adhesive disposed upon the generally flat bottom, the adhesive protected by a removable cover;

a needle hub disposed within the central region, the needle hub receiving a flexible tubing line generally parallel to the generally flat bottom and providing a needle extending generally normal to the generally flat bottom from the middle area of the central region, the needle extending for a first length;

a removable needle cover initially disposed about the needle, the removable needle cover structured and arranged to removably engage with the needle hub; and a closing system structured and arranged to close the first side member and the second side member of the flexible member about the needle.

2. The butterfly needle assembly of claim 1, wherein the closing system is provided by a button disposed upon the generally flat bottom proximate to a first distal edge of the first side member and a through-hole disposed proximate to a second distal edge of the second side member.

3. The butterfly needle assembly of claim 1, wherein the first side member and the second side member have substantially the same second length from the central region, the second length greater than the first length.

4. The butterfly needle assembly of claim 1, wherein the removable needle cover has a first end disposed through the generally flat bottom into the needle hub, the first end having opposing side tabs structured and arranged to rotatably lock into the needle hub.

5. The butterfly needle assembly of claim 1, wherein the removable needle cover when engaged to the needle hub hermetically seals the needle.

6. The butterfly needle assembly of claim 1, wherein the removable needle cover when engaged to the needle hub provides a sealed space about the needle.

7. The butterfly needle assembly of claim 1, wherein the snap-in needle structure has opposing side ridges structured and arranged to snap under corresponding ridges of the needle hub.

8. The butterfly needle assembly of claim 1, wherein the needle hub is provided by at least two elements, a needle hub frame united with the flexible member opposite from the adhesive and a snap-in needle structure, the snap-in needle structure provided by a duct member structured and arranged to join with the flexible tubing at a first end and to join with a needle at a second end, the second end generally normal to the first end, the duct member further structured and arranged for snap-in binding with the needle hub frame.

9. The butterfly needle assembly of claim 8, wherein a first butterfly needle assembly is provided by a first snap-in needle structure providing a first needle with a first gauge, and a second butterfly needle assembly is provided by a second snap-in needle structure providing a second needle with a second gauge, the second gauge different from the first gauge.

10. The butterfly needle assembly of claim 1, wherein the needle is a straight needle.

11. The butterfly needle assembly of claim 1, wherein the flexible tubing line is flow control tubing with a luer connector structured and arranged for connection to a liquid source.

12. The butterfly needle assembly of claim 1, wherein the flexible member has at plurality of bend grooves evenly disposed on either side of the needle hub and normal to the needle, the bend grooves facilitating the closing of the first side member and the second side member about the needle.

13. The butterfly needle assembly of claim 1, wherein the butterfly needle assembly is disposed in a sealed package and irradiated to sterilize the butterfly needle assembly.

14. The butterfly needle assembly of claim 1, wherein the needle hub has an elevated finger gripper.

15. The butterfly needle assembly of claim 1, wherein the butterfly assembly is structured and arranged to engage with a needle insertion device.

16. A butterfly needle assembly, comprising:

a flexible member having a central region with a first side member and a second side member collectively providing a generally flat bottom;

an adhesive disposed upon the generally flat bottom, the adhesive protected by a removable cover;

a needle hub frame united with the flexible member opposite from the adhesive;

a snap-in needle structure provided by a duct member having a first end and a second end, the first end joined with a flexible tubing line and the second end joined with a needle having a first length, the second end generally normal to the first end, the duct member further structured and arranged for snap-in binding with the needle hub frame, the needle extending generally normal to the generally flat bottom from a middle area of the central region, the flexible tubing generally parallel to the generally flat bottom proximate to the first end of the duct member; and a removable needle cover initially disposed about the needle, the removable needle cover structured and arranged to removably engage with the needle hub frame; and a closing system structured and arranged to the first side member and the second side member of the flexible member about the needle.

17. The butterfly needle assembly of claim 16, wherein the closing system is provided by button disposed upon the generally flat bottom proximate to a first distal edge of the first side member and a through-hole disposed proximate to a second distal edge of the second side member.

18. The butterfly needle assembly of claim 16, wherein the first side member and the second side member have substantially the same second length from the central region, the second length greater than the first length.

19. The butterfly needle assembly of claim 16, wherein the removable needle cover has a first end disposed through the generally flat bottom into the needle hub, the first end having opposing side tabs structured and arranged to rotatably lock into the needle hub.

20. The butterfly needle assembly of claim 16, wherein the removable needle cover when engaged to the needle hub hermetically seals the needle.

21. The butterfly needle assembly of claim 16, wherein the removable needle cover when engaged to the needle hub provides a sealed space about the needle.

22. The butterfly needle assembly of claim 16, wherein the snap-in needle structure has opposing side ridges structured and arranged to snap under corresponding ridges of the needle hub.

23. The butterfly needle assembly of claim 16, wherein a first butterfly needle assembly is provided by a first snap-in needle structure providing a first needle with a first gauge, and a second butterfly needle assembly is provided by a second snap-in needle structure providing a second needle with a second gauge, the second gauge different from the first gauge.

24. The butterfly needle assembly of claim 16, wherein the needle is a straight needle.

25. The butterfly needle assembly of claim 16, wherein the flexible tubing line is flow control tubing with a luer connector structured and arranged for connection to a liquid source.

26. The butterfly needle assembly of claim 16, wherein the flexible member has a plurality of bend grooves evenly disposed on either side of the needle hub and normal to the needle, the bend grooves facilitating the closing of the first side member and the second side member about the needle.

27. The butterfly needle assembly of claim 16, wherein the butterfly needle assembly is disposed in a sealed package and irradiated to sterilize the butterfly needle assembly.

28. A butterfly needle assembly, comprising:

a flexible member having a central region with a first side member and a second side member collectively providing a generally flat bottom, a button disposed upon the generally flat bottom proximate to a first distal edge of the first side member and a through-hole disposed proximate to a second distal edge of the second side member, the button and through-hole collectively providing a closing system structured and arranged to close the first side member and the second side member of the flexible member about the needle;

an adhesive disposed upon the generally flat bottom, the adhesive protected by a removable cover;

a needle hub frame united with the flexible member opposite from the adhesive;

a snap-in needle structure provided by a duct member having a first end and a second end, the first end joined with a flexible tubing line and the second end joined with a needle having a first length, the second end generally normal to the first end, the duct member further structured and arranged for snap-in binding with the needle hub frame, the needle extending generally normal to the generally flat bottom from the central region, the flexible tubing generally parallel to the generally flat bottom proximate to the first end of the duct member; and a removable needle cover initially disposed about the needle, the removable needle cover having a first end disposed through the generally flat bottom into the needle hub frame, the first end having opposing side tabs structured and arranged to rotatably lock into the needle hub frame.

29. The butterfly needle assembly of claim 28, wherein the first side member and the second side member have substantially the same second length from the central region, the second length greater than the first length.

30. The butterfly needle assembly of claim 28, wherein a first butterfly needle assembly is provided by a first snap-in needle structure providing a first needle with a first gauge, and a second butterfly needle assembly is provided by a second snap-in needle structure providing a second needle with a second gauge, the second gauge different from the first gauge.

31. The butterfly needle assembly of claim 28, wherein the needle is a straight needle.

32. The butterfly needle assembly of claim 28, wherein the removable needle cover when engaged to the needle hub provides a sealed space about the needle.

33. The butterfly needle assembly of claim 28, wherein the snap-in needle structure has opposing side ridges structured and arranged to snap under corresponding ridges of the needle hub.

34. The butterfly needle assembly of claim 28, wherein the flexible tubing line is flow control tubing with a luer connector structured and arranged for connection to a liquid source.

35. The butterfly needle assembly of claim 28, wherein the flexible tubing line is flow control tubing with a luer connector structured and arranged for connection to a liquid source.

36. The butterfly needle assembly of claim 28, wherein the flexible member has at plurality of bend grooves evenly disposed on either side of the needle hub and normal to the needle, the bend grooves facilitating the closing of the first side member and the second side member about the needle.

37. The butterfly needle assembly of claim 28, wherein the butterfly needle assembly is disposed in a sealed package and irradiated to sterilize the butterfly needle assembly.

38. A method of providing a butterfly needle assembly, comprising:

providing a flexible member having a central region with a first side member and a second side member collectively providing a generally flat bottom, the central region having a middle area;

providing a dressing upon the generally flat bottom, the adhesive protected by a removable cover;

providing a needle hub disposed within the central region, the needle hub receiving a flexible tubing line generally parallel to the generally flat bottom and providing a needle extending generally normal to the generally flat bottom from the middle area of the central region, the needle extending for a first length;

providing a removable needle cover initially disposed about the needle, the removable needle cover structured and arranged to removably engage with the needle hub; and providing a closing system structured and arranged to close the first side member and the second side member of the flexible member about the needle.

39. The method of claim 38, wherein the closing system is provided by a button disposed upon the generally flat bottom proximate to a first distal edge of the first side member and a through-hole disposed proximate to a second distal edge of the second side member.

40. The method of claim 38, wherein the first side member and the second side member have substantially the same second length from the central region, the second length greater than the first length.

41. The method of claim 38, wherein the removable needle cover has a first end disposed through the generally flat bottom into the needle hub, the first end having opposing side tabs structured and arranged to rotatably lock into the needle hub.

42. The method of claim 38, wherein the snap-in needle structure has opposing side ridges structured and arranged to snap under corresponding ridges of the needle hub.

43. The method of claim 38, wherein the removable needle cover when engaged to the needle hub provides a sealed space about the needle.

44. The method of claim 38, wherein the needle hub is provided by at least two elements, a needle hub frame united with the flexible member opposite from the adhesive and a snap-in needle structure, the snap-in needle structure provided by a duct member structured and arranged to join with the flexible tubing at a first end and to join with a needle at a second end, the second end generally normal to the first end, the duct member further structured and arranged for snap-in binding with the needle hub frame.

45. The method of claim 44, wherein a first butterfly needle assembly is provided by a first snap-in needle structure providing a first needle with a first gauge, and a second butterfly needle assembly is provided by a second snap-in needle structure providing a second needle with a second gauge, the second gauge different from the first gauge.

46. The method of claim 38, wherein the needle is a straight needle.

47. The method of claim 38, wherein the flexible tubing line is flow control tubing with a luer connector structured and arranged for connection to a liquid source.

48. The method of claim 38, wherein the flexible member has a plurality of bend grooves evenly disposed on either side of the needle hub and normal to the needle, the bend grooves facilitating the closing of the first side member and the second side member about the needle.

49. The method of claim 38, wherein the butterfly needle assembly is disposed in a sealed package and irradiated to sterilize the butterfly needle assembly.

\* \* \* \* \*